US006596847B2

(12) United States Patent
Kelley et al.

(10) Patent No.: US 6,596,847 B2
(45) **Date of Patent: *Jul. 22, 2003**

(54) TISSUE FACTOR PROTEIN VARIANTS

(75) Inventors: Robert F. Kelley, San Bruno, CA (US); Geoffrey F. Lee, Boulder, CO (US)

(73) Assignee: Genentech, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/355,000

(22) Filed: Jul. 14, 1999

(65) Prior Publication Data

US 2002/0142373 A1 Oct. 3, 2002

Related U.S. Application Data

(60) Provisional application No. 60/092,937, filed on Jul. 15, 1998, and provisional application No. 60/098,367, filed on Aug. 28, 1998.

(51) Int. Cl.[7] ........................ A61K 35/14; A61K 38/16; C07K 1/00; C07K 14/00; C07K 17/00

(52) U.S. Cl. ........................................ 530/380; 530/350

(58) Field of Search ................................ 530/350, 384, 530/380, 381; 514/2

(56) References Cited

U.S. PATENT DOCUMENTS

| | | | |
|---|---|---|---|
| 5,223,427 | A | 6/1993 | Edgington et al. |
| 5,346,991 | A | 9/1994 | Roy et al. |
| 5,504,067 | A | 4/1996 | Morrissey et al. |
| 5,726,147 | A | 3/1998 | Ruf et al. |
| 6,093,399 | A | 7/2000 | Thorpe et al. |

FOREIGN PATENT DOCUMENTS

| | | |
|---|---|---|
| EP | 266993 | 5/1988 |
| WO | WO 89/02922 | 4/1989 |
| WO | WO 94/07515 | 4/1994 |
| WO | WO 94/28017 | 12/1994 |
| WO | WO 96/40921 | 12/1996 |
| WO | WO 97/19357 | 5/1997 |
| WO | WO 97/20939 | 6/1997 |

OTHER PUBLICATIONS

Kelly et al., "Tissue factor residue Asp44 regulates catalytic function of the bound proteinase Factor VIIa" (Medline abstract; accession #96207575) (Apr. 1, 1996).

Andrews et al., "Conservation of tissue factor primary sequence among three mammalian species" *Gene* 98:265–269 (1991).

Bach et al., "Factor VII Binding to Tissue Factor in Reconstituted Phospholipid Vesicles: Induction of Cooperativity by Phosphatidylserine" *Biochemistry* 25(14):4007–4020 (1986).

Bach, R. R., "Initiation of Coagulation by Tissue Factor" *CRC Critical Reviews in Biochemistry* 23(4):339–368 (1988).

Badimon et al., "Hirudin and Other Thrombin Inhibitors: Experimental Results and Potential Clinical Applications" *Trends Cardiovasc. Med.* 1(6):261–267 (1991).

Banner et al., "The crystal structure of the complex of blood coagulation factor VIIa with soluble tissue factor" *Nature* 380:41–46 (Mar. 7, 1996).

Biemond et al., "Complete Inhibition of Endotoxin–Induced Coagulation Activation in Chimpanzees with a Monoclonal Fab Fragment against Factor VII/VIIa" *Thrombosis Haemostasis* 73(2):223–230 (1995).

Bone, R. C., "Modulators of Coagulation: A Critical Appraisal of Their Role In Sepsis" *Arch Intern Med* 152:1381–1389 (Jul. 1992).

Bromberg et al., "Tissue factor promotes melanoma metastasis by a pathway independent of blood coagulation" *Proc. Natl. Acad. Sci. USA* 92:8205–8209 (Aug. 1995).

Carson et al., "The role of tissue factor in the production of thrombin" *Blood. Coag. Fibrinol* 4:281–292 (1993).

Colman, R. W., "The Role of Plasma Proteases In Septic Shock" *The New England J. of Med.* 320(18):1207–1209 (May 4, 1989).

Creasey et al., "Tissue Factor Pathway Inhibitor Reduces Mortality from *Escherichia coli* Septic Shock" *J. Clin. Invest.* 91:2850–2860 (Jun. 1993).

Davie et al., "The Coagulation Cascade: Initiation, Maintenance, and Regulation" *Biochemistry* 30(43):10363–10370 (Oct. 29, 1991).

Drake et al., "Functional Tissue Factor Is Entirely Cell Surface Expressed on Lipopolysaccharide–stimulated Human Blood Monocytes and a Constitutively Tissue Factor–producing Neoplastic Cell Line" *Journal of Cell Biology* 109:389–395 (Jul. 1989).

Fisher et al., "Cloning and Expression of Human Tissue Factor cDNA" *Thrombosis Research* 48(1):89–99 (1987).

Gibbs et al., "Identification of the Factor VIIa Binding Site on Tissue Factor by Homologous Loop Swap and Alanine Scanning Mutagenesis" *Biochemistry* 33(47):14003–14010 (1994).

Harlos et al., "Crystal structure of the extracellular region of human tissue factor" *Nature* 370:662–666 (Aug. 25, 1994).

(List continued on next page.)

*Primary Examiner*—Gary Kunz
*Assistant Examiner*—Robert S. Landsman
(74) *Attorney, Agent, or Firm*—Merchant & Gould P.C.

(57) ABSTRACT

The invention provides amino acid sequence variants of tissue factor protein. The tissue factor protein variants have a greater affinity for Factor VII/VIIa than wild-type counterparts. The invention also provides pharmaceutical compositions comprising the novel compositions as well as their use in diagnostic, therapeutic, and prophylactic methods.

41 Claims, 3 Drawing Sheets

OTHER PUBLICATIONS

Hartzell et al., "A Growth Factor–Responsive Gene of Murine BALB/c 3T3 Cells Encodes a Protein Homologous to Human Tissue Factor" *Molecular & Cellular Biology* 9(6):2567–2573 (Jun. 1989).

Haskel et al., "Prevention of Arterial Reocclusion After Thrombolysis With Recombinant Lipoprotein–Associated Coagulation Inhibitor" *Circulation* 84(2):821–827 (Aug. 1991).

Holst et al., "Antithrombotic Properties of a Truncated Recombinant Tissue Factor Pathway Inhibitor in an Experimental Venous Thrombosis Model" *Haemostasis* 23(Suppl. 1):112–117 (1993).

Kelley et al., "A Soluble Tissue Factor Mutant Is a Selective Anticoagulant and Antithrombotic Agent" *Blood* 89(9):3219–3227 (May 1, 1997).

Kelley et al., "Analysis of the Factor VIIa Binding Site on Human Tissue Factor: Effects of Tissue Factor Mutations on the Kinetics and Thermodynamics of Binding" *Biochemistry* 34(33):10383–10392 (1995).

Lee et al., "A Novel Soluble Tissue Factor Variant with an Altered Factor VIIa Binding Interface" *Journal of Biological Chemistry* 273(7):4149–4154 (Feb. 13, 1998).

Lee et al., "Potent Bifunctional Anticoagulants: Kunitz Domain–Tissue Factor Fusion Proteins" *Biochemistry* 36(19):5607–5611 (May 13, 1997).

Lowman and Wells, "Affinity maturation of human growth hormone by monovalent phage display" *Journal of Molecular Biology* 234(3):564–578 (Dec. 5, 1993).

Lowman et al., "Selecting High–Affinity Binding Proteins by Monovalent Phage Display" *Biochemistry* 30(45):10832–10838 (1991).

Mimms et al., "Phospholipid Vesicle Formation and Transmembrane Protein Incorporation Using Octyl Glucoside" *Biochemistry* 20(4):833–840 (1981).

Muller et al., "Structure of the Extracellular Domain of Human Tissue Factor: Location of the Factor VIIa Binding Site" *Biochemistry* 33(36):10864–10870 (1994).

O'Brien et al., "Factor VIII–Bypassing Activity of Bovine Tissue Factor Using the Canine Hemophilic Model" *J. Clin. Invest.* 82:206–211 (Jul. 1988).

Paborsky et al., "Mammalian Cell Transient Expression of Tissue Factor for the Production of Antigen" *Protein Eng.* 3(6):547–553 (1990).

Paborsky et al., "Purification of Recombinant Human Tissue Factor" *Biochemistry* 28(20):8072–8077 (1989).

Pawashe et al., "A Monoclonal Antibody Against Rabbit Tissue Factor Inhibits Thrombus Formation in Stenotic Injured Rabbit Carotid Arteries" *Circ. Res.* 74(1):56–63 (Jan. 1994).

Rao et al., "Tissue Factor Residues $Lys^{165}$ and $Lys^{166}$ Are Essential for Rapid Formation of the Quaternary Complex of Tissue Factor–VIIa with Xa–Tissue Factor Pathway Inhibitor" *Biochemistry* 34(34):10867–10871 (1995).

Rapaport et al., "Initiation and Regulation of Tissue Factor–Dependent Blood Coagulation" *Arterioscler. Thromb.* 12(10):1111–1121 (Oct. 1992).

Roy et al., "Lysine Residues 165 and 166 Are Essential for the Cofactor Function of Tissue Factor" *Journal of Biological Chemistry* 266(32):22063–22066 (Nov. 15, 1991).

Roy et al., "Self–association of Tissue Factor as Revealed by Chemical Cross–linking" *Journal of Biological Chemistry* 266(8):4665–4668 (Mar. 15, 1991).

Ruf et al., "Cofactor Residues Lysine 165 and 166 Are Critical for Protein Substrate Recognition by the Tissue Factor–Factor VIIa Protease Complex" *Journal of Biological Chemistry* 267(9):6375–6381 (Mar. 25, 1992).

Ruf et al., "Mutational Mapping of Functional Residues in Tissue Factor: Identification of Factor VII Recognition Determinants in Both Structural Modules of the Predicted Cytokine Receptor Homology Domain" *Biochemistry* 33(6):1565–1572 (1994).

Ruf et al., "Phospholipid–independent and –dependent Interactions Required for Tissue Factor Receptor and Cofactor Function" *Journal of Biological Chemistry* 266(4):2158–2166 (Feb. 5, 1991).

Ruf et al., "Tissue Factor Residues 157–167 Are Required for Efficient Proteolytic Activation of Factor X and Factor VII" *Journal of Biological Chemistry* 267(31):22206–22210 (Nov. 5, 1992).

Schullek et al., "Key Ligand Interface Residues in Tissue Factor Contribute Independently to Factor VIIa Binding" *Journal of Biological Chemistry* 269(30):19399–19403 (Jul. 29, 1994).

Shigematsu et al., "Expression of Human Soluble Tissue Factor in Yeast and Enzymatic Properties of Its Complex with Factor VIIa" *Journal of Biological Chemistry* 267(30):21329–21337 (Oct. 25, 1992).

Smith, G. P., "Surface presentation of protein epitopes using bacteriophage expression systems" *Curr. Opin. Biotechnol.* 2(5):668–673 (1991).

Takayenoki et al., "cDNA and Amino Acid Sequences of Bovine Tissue Factor" *Biochem. & Biophys. Res. Comm.* 181(3):1145–1150 (Dec. 31, 1991).

Taylor, Jr. et al., "Lethal *E. coli* Septic Shock Is Prevented by Blocking Tissue Factor With Monoclonal Antibody" *Circ. Shock* 33(3):127–134 (Mar. 1991).

Warr et al., "Disseminated Intravascular Coagulation in Rabbits Induced by Administration of Endotoxin or Tissue Factor: Effect of Anti–Tissue Factor Antibodies and Measurement of Plasma Extrinsic Pathway Inhibitor Activity" *Blood* 75(7):1481–1489 (Apr. 1, 1990).

Waxman et al., "Tissue Factor and Its Extracellular Soluble Domain: The Relationship between Intermolecular Association with Factor VIIa and Enzymatic Activity of the Complex" *Biochemistry* 31(16):3998–4003 (1992).

Wells, J. A., "Additivity of Mutational Effects in Proteins" *Biochemistry* 29(37):8509–8517 (Sep. 18, 1990).

Wilcox et al., "Localization of Tissue Factor in the Normal Vessel Wall and in the Atherosclerotic Plaque" *Proc. Natl. Acad. Sci. USA* 86:2839–2843 (Apr. 1989).

Dickinson and Ruf, "Active Site Modification of Factor VIIa Affects Interactions of the Protease Domain with Tissue Factor", *Journal of Biological Chemistry*, 272(32): 19975–19879 (Aug. 1997).

Dickinson et al., "Identification of surface residues mediating tissue factor binding and catalytic function of the serine protease factor VIIa", *Proc. Natl. Acad. Sci. USA*, 93:14379–14384 (Dec. 1996).

Eaton et al., "Construction and characterization of an active factor VIII variant lacking the central one–third of the molecule", *Biochemistry*, 25:8343–8347 (1986).

Golino et al., "Effects of tissue factor induced by oxygen free radicals on coronary flow during reperfusion", *Nature Medicine*, 2:35–40 (1996).

Huang et al., "Substrate Recognition by Tissue Factor–Factor VIIa", *Journal of Biological Chemistry*, 271(36):21752–21757 (Sep. 1996).

Huang et al., "The Mechanism of an Inhibitory Antibody on TF–initiated Blood Coagulation Revealed by the Crystal Structure of Human Tissue Factor, Fab 5G9 and TF 5G9 Complex", *J. Mol. Biol.*, 275:873–894 (1998).

Kirchhofer et al., "Active Site–Blocked Factors VIIa and IXa Differentially Inhibit Fibrin Formation in a Human Ex Vivo Thrombosis Model", *Arterioscler. Thromb. Vasc. Biol.*, 15(8):1098–1106 (Aug. 1995).

Kirchhofer et al., "Molecular and Structural Advances in Tissue Factor–Dependent Coagulation", *Elsevier Science* (Trends in Cardiovascular) 7(8):316–324 (Nov. 1997).

Kirchhofer et al., "Anticoagulant Activity of Different Tissue Factor/Factor VIIa Inhibitors in a Human Ex–Vivo Thrombosis Model", *Blood*, (Suppl. 1) 86(10):91a (Nov. 15, 1995).

Martin et al., "Synthesis and Characterization of Wild–Type and Variant γ–Carboxyglucamic Acid–Containing Domains of Factor VII", *Biochemistry*, 32:13949–13955 (1993).

McCallum et al., "Tissue Factor Positions and Maintains the Factor VIIa Active Site Far Above the Membrane Surface Even in the Absence of the Factor VIIa Gla Domain", *Journal of Biological Chemistry*, 272:30160–30166 (Nov. 1997).

Morrissey et al., "Molecular Cloning of the cDNA for Tissue Factor, the Cellular Receptor for the Initiation of the Coagulation Protease Cascade", *Cell*, 50(1): 129–135 (1987).

SEQUENCE LISTING

<160> NUMBER OF SEQ ID NOS: 10

<210> SEQ ID NO 1
<211> LENGTH: 263
<212> TYPE: PRT
<213> ORGANISM: Homo sapiens -continued

<400> SEQUENCE: 1

```
Ser Gly Thr Thr Asn Thr Val Ala Ala Tyr Asn Leu Thr Trp Lys
  1               5                  10                  15

Ser Thr Asn Phe Lys Thr Ile Leu Glu Trp Glu Pro Lys Pro Val
                 20                  25                  30

Asn Gln Val Tyr Thr Val Gln Ile Ser Thr Lys Ser Gly Asp Trp
                 35                  40                  45

Lys Ser Lys Cys Phe Tyr Thr Thr Asp Thr Glu Cys Asp Leu Thr
                 50                  55                  60

Asp Glu Ile Val Lys Asp Val Lys Gln Thr Tyr Leu Ala Arg Val
                 65                  70                  75

Phe Ser Tyr Pro Ala Gly Asn Val Glu Ser Thr Gly Ser Ala Gly
                 80                  85                  90

Glu Pro Leu Tyr Glu Asn Ser Pro Glu Phe Thr Pro Tyr Leu Glu
                 95                 100                 105

Thr Asn Leu Gly Gln Pro Thr Ile Gln Ser Phe Glu Gln Val Gly
                110                 115                 120

Thr Lys Val Asn Val Thr Val Glu Asp Glu Arg Thr Leu Val Arg
                125                 130                 135

Arg Asn Asn Thr Phe Leu Ser Leu Arg Asp Val Phe Gly Lys Asp
                140                 145                 150

Leu Ile Tyr Thr Leu Tyr Tyr Trp Lys Ser Ser Ser Ser Gly Lys
                155                 160                 165

Lys Thr Ala Lys Thr Asn Thr Asn Glu Phe Leu Ile Asp Val Asp
                170                 175                 180

Lys Gly Glu Asn Tyr Cys Phe Ser Val Gln Ala Val Ile Pro Ser
                185                 190                 195

Arg Thr Val Asn Arg Lys Ser Thr Asp Ser Pro Val Glu Cys Met
                200                 205                 210

Gly Gln Glu Lys Gly Glu Phe Arg Glu Ile Phe Tyr Ile Ile Gly
                215                 220                 225

Ala Val Val Phe Val Val Ile Ile Leu Val Ile Ile Leu Ala Ile
                230                 235                 240

Ser Leu His Lys Cys Arg Lys Ala Gly Val Gly Gln Ser Trp Lys
                245                 250                 255

Glu Asn Ser Pro Leu Asn Val Ser
                260         263
```

<210> SEQ ID NO 2
<211> LENGTH: 219
<212> TYPE: PRT
<213> ORGANISM: Homo sapiens

<400> SEQUENCE: 2

```
Ser Gly Thr Thr Asn Thr Val Ala Ala Tyr Asn Leu Thr Trp Lys
  1               5                  10                  15

Ser Thr Asn Phe Lys Thr Ile Leu Glu Trp Glu Pro Lys Pro Val
                 20                  25                  30

Asn Gln Val Tyr Thr Val Gln Ile Ser Thr Lys Ser Gly Asp Trp
                 35                  40                  45

Lys Ser Lys Cys Phe Tyr Thr Thr Asp Thr Glu Cys Asp Leu Thr
                 50                  55                  60

Asp Glu Ile Val Lys Asp Val Lys Gln Thr Tyr Leu Ala Arg Val
                 65                  70                  75
```

-continued

```
Phe Ser Tyr Pro Ala Gly Asn Val Glu Ser Thr Gly Ser Ala Gly
                80                  85                  90

Glu Pro Leu Tyr Glu Asn Ser Pro Glu Phe Thr Pro Tyr Leu Glu
                95                 100                 105

Thr Asn Leu Gly Gln Pro Thr Ile Gln Ser Phe Glu Gln Val Gly
               110                 115                 120

Thr Lys Val Asn Val Thr Val Glu Asp Glu Arg Thr Leu Val Arg
               125                 130                 135

Arg Asn Asn Thr Phe Leu Ser Leu Arg Asp Val Phe Gly Lys Asp
               140                 145                 150

Leu Ile Tyr Thr Leu Tyr Tyr Trp Lys Ser Ser Ser Ser Gly Lys
               155                 160                 165

Lys Thr Ala Lys Thr Asn Thr Asn Glu Phe Leu Ile Asp Val Asp
               170                 175                 180

Lys Gly Glu Asn Tyr Cys Phe Ser Val Gln Ala Val Ile Pro Ser
               185                 190                 195

Arg Thr Val Asn Arg Lys Ser Thr Asp Ser Pro Val Glu Cys Met
               200                 205                 210

Gly Gln Glu Lys Gly Glu Phe Arg Glu
               215                 219


<210> SEQ ID NO 3
<211> LENGTH: 219
<212> TYPE: PRT
<213> ORGANISM: Artificial sequence
<220> FEATURE:
<221> NAME/KEY: Artificial sequence
<222> LOCATION: 219
<223> OTHER INFORMATION: human tissue factor sequence variant

<400> SEQUENCE: 3

Ser Gly Thr Thr Asn Thr Val Ala Ala Tyr Asn Leu Thr Trp Lys
  1               5                  10                  15

Ser Thr Asn Phe Lys Thr Ile Leu Glu Trp Glu Pro Lys Pro Val
                 20                  25                  30

Asn Gln Val Tyr Thr Val Gln Ile Ser Thr Lys Ser Gly Asp Trp
                 35                  40                  45

Lys Ser Lys Cys Phe Tyr Thr Thr Asp Thr Glu Cys Asp Leu Thr
                 50                  55                  60

Asp Glu Ile Val Lys Asp Val Lys Gln Thr Tyr Leu Ala Arg Val
                 65                  70                  75

Phe Ser Tyr Pro Ala Gly Asn Val Glu Ser Thr Gly Ser Ala Gly
                 80                  85                  90

Glu Pro Leu Tyr Glu Asn Ser Pro Glu Phe Thr Pro Tyr Leu Glu
                 95                 100                 105

Thr Asn Leu Gly Gln Pro Thr Ile Gln Ser Phe Glu Gln Val Gly
                110                 115                 120

Thr Lys Val Asn Val Thr Val Glu Asp Glu Arg Thr Leu Val Arg
                125                 130                 135

Arg Asn Asn Thr Phe Leu Ser Leu Arg Asp Val Phe Gly Lys Asp
                140                 145                 150

Leu Ile Tyr Thr Leu Tyr Tyr Trp Lys Ser Ser Ser Ser Gly Ala
                155                 160                 165

Ala Thr Ala Lys Thr Asn Thr Asn Glu Phe Leu Ile Asp Val Asp
                170                 175                 180
```

-continued

```
Lys Gly Glu Asn Tyr Cys Phe Ser Val Gln Ala Val Ile Pro Ser
                185                 190                 195

Arg Thr Val Asn Arg Lys Ser Thr Asp Ser Pro Val Glu Cys Met
                200                 205                 210

Gly Gln Glu Lys Gly Glu Phe Arg Glu
                215             219


<210> SEQ ID NO 4
<211> LENGTH: 219
<212> TYPE: PRT
<213> ORGANISM: Artificial Sequence
<220> FEATURE:
<221> NAME/KEY: Artificial sequence
<222> LOCATION: 1-219
<223> OTHER INFORMATION: human tissue factor sequence variant

<400> SEQUENCE: 4

Ser Gly Thr Thr Asn Thr Val Ala Ala Tyr Asn Leu Thr Trp Ala
  1               5                  10                  15

Ser Thr Asn Phe Lys Thr Ile Leu Glu Trp Glu Pro Lys Pro Val
                 20                  25                  30

Asn Gln Val Tyr Thr Val Gln Ile Ser Thr Lys Ser Gly Asp Trp
                 35                  40                  45

Lys Ser Lys Cys Phe Tyr Thr Thr Asp Thr Glu Cys Asp Leu Thr
                 50                  55                  60

Asp Glu Ile Val Lys Asp Val Lys Gln Thr Tyr Leu Ala Arg Val
                 65                  70                  75

Phe Ser Tyr Pro Ala Gly Asn Val Glu Ser Thr Gly Ser Ala Gly
                 80                  85                  90

Glu Pro Leu Tyr Glu Asn Ser Pro Glu Phe Thr Pro Tyr Leu Glu
                 95                 100                 105

Thr Asn Leu Gly Gln Pro Thr Ile Gln Ser Phe Glu Gln Val Gly
                110                 115                 120

Thr Lys Val Asn Val Thr Val Glu Asp Glu Arg Thr Leu Val Arg
                125                 130                 135

Arg Asn Asn Thr Phe Leu Ser Leu Arg Asp Val Phe Gly Lys Asp
                140                 145                 150

Leu Ile Tyr Thr Leu Tyr Tyr Trp Lys Ser Ser Ser Ser Gly Ala
                155                 160                 165

Ala Thr Ala Lys Thr Asn Thr Asn Glu Phe Leu Ile Asp Val Asp
                170                 175                 180

Lys Gly Glu Asn Tyr Cys Phe Ser Val Gln Ala Val Ile Pro Ser
                185                 190                 195

Arg Thr Val Asn Arg Lys Ser Thr Asp Ser Pro Val Glu Cys Met
                200                 205                 210

Gly Gln Glu Lys Gly Glu Phe Arg Glu
                215             219


<210> SEQ ID NO 5
<211> LENGTH: 219
<212> TYPE: PRT
<213> ORGANISM: Artificial Sequence
<220> FEATURE:
<221> NAME/KEY: Artificial sequence
<222> LOCATION: 1-219
<223> OTHER INFORMATION: human tissue factor sequence variant

<400> SEQUENCE: 5

Ser Gly Thr Thr Asn Thr Val Ala Ala Tyr Asn Leu Thr Trp Lys
```

-continued

```
  1               5                  10                  15

Ser Thr Asn Phe Lys Thr Ile Leu Glu Trp Glu Pro Lys Pro Val
                20                  25                  30

Asn Gln Val Tyr Thr Val Gln Ile Ser Thr Lys Ser Gly Asp Trp
                35                  40                  45

Lys Ser Lys Cys Phe Tyr Thr Thr Ser Thr Glu Cys Asp Leu Thr
                50                  55                  60

Asp Glu Ile Val Lys Asp Val Lys Gln Thr Tyr Leu Ala Arg Val
                65                  70                  75

Phe Ser Tyr Pro Ala Gly Asn Val Glu Ser Thr Gly Ser Ala Gly
                80                  85                  90

Glu Pro Leu Tyr Glu Asn Ser Pro Glu Phe Thr Pro Tyr Leu Glu
                95                 100                 105

Thr Asn Leu Gly Gln Pro Thr Ile Gln Ser Phe Glu Gln Val Gly
               110                 115                 120

Thr Lys Val Asn Val Thr Val Glu Asp Glu Arg Thr Leu Val Arg
               125                 130                 135

Arg Asn Asn Thr Phe Leu Ser Leu Arg Asp Val Phe Gly Lys Asp
               140                 145                 150

Leu Ile Tyr Thr Leu Tyr Tyr Trp Lys Ser Ser Ser Ser Gly Ala
               155                 160                 165

Ala Thr Ala Lys Thr Asn Thr Asn Glu Phe Leu Ile Asp Val Asp
               170                 175                 180

Lys Gly Glu Asn Tyr Cys Phe Ser Val Gln Ala Val Ile Pro Ser
               185                 190                 195

Arg Thr Val Asn Arg Lys Ser Thr Asp Ser Pro Val Glu Cys Met
               200                 205                 210

Gly Gln Glu Lys Gly Glu Phe Arg Glu
               215             219


<210> SEQ ID NO 6
<211> LENGTH: 219
<212> TYPE: PRT
<213> ORGANISM: Artificial Sequence
<220> FEATURE:
<221> NAME/KEY: Artificial sequence
<222> LOCATION: 1-219
<223> OTHER INFORMATION: human tissue factor sequence variant

<400> SEQUENCE: 6

Ser Gly Thr Thr Asn Thr Val Ala Ala Tyr Asn Leu Thr Trp Lys
  1               5                  10                  15

Ser Thr Asn Phe Lys Thr Ile Leu Glu Trp Glu Pro Lys Pro Val
                20                  25                  30

Asn Gln Val Tyr Thr Val Gln Ile Ser Thr Lys Ser Gly Asp Trp
                35                  40                  45

Lys Ser Lys Cys Phe Tyr Thr Thr Asp Thr Glu Cys Asp Leu Thr
                50                  55                  60

Asp Glu Ile Val Lys Asp Val Lys Gln Thr Tyr Leu Ala Arg Val
                65                  70                  75

Phe Ser Tyr Pro Ala Gly Asn Val Glu Ser Thr Gly Ser Ala Gly
                80                  85                  90

Glu Pro Leu Tyr Glu Asn Ser Pro Glu Phe Thr Pro Tyr Leu Glu
                95                 100                 105

Thr Asn Leu Gly Gln Pro Thr Ile Gln Ser Phe Glu Gln Val Gly
               110                 115                 120
```

-continued

```
Thr Lys Val Asn Val Thr Val Glu Asp Glu Arg Thr Leu Val Arg
                125                 130                 135

Arg Asn Asn Thr Phe Leu Ser Leu Arg Asp Val Phe Gly Lys Asp
                140                 145                 150

Leu Ile Tyr Thr Leu Tyr Tyr Trp Lys Ser Ser Ser Ser Gly Ala
                155                 160                 165

Ala Thr Ala Lys Thr Asn Thr Asn Glu Phe Leu Ile Asp Val Asp
                170                 175                 180

Lys Gly Glu Asn Ala Cys Phe Ser Val Gln Ala Val Ile Pro Ser
                185                 190                 195

Arg Thr Val Asn Arg Lys Ser Thr Asp Ser Pro Val Glu Cys Met
                200                 205                 210

Gly Gln Glu Lys Gly Glu Phe Arg Glu
                215             219


<210> SEQ ID NO 7
<211> LENGTH: 219
<212> TYPE: PRT
<213> ORGANISM: Artificial Sequence
<220> FEATURE:
<221> NAME/KEY: Artificial sequence
<222> LOCATION: 1-219
<223> OTHER INFORMATION: human tissue factor sequence variant

<400> SEQUENCE: 7

Ser Gly Thr Thr Asn Thr Val Ala Ala Tyr Asn Leu Thr Trp Lys
  1               5                  10                  15

Ser Thr Asn Phe Lys Thr Ile Leu Glu Trp Glu Pro Lys Pro Val
                 20                  25                  30

Asn Gln Val Tyr Thr Val Gln Ile Ser Thr Lys Ser Gly Asp Trp
                 35                  40                  45

Lys Ser Lys Cys Phe Tyr Thr Thr Asp Thr Glu Cys Asp Leu Thr
                 50                  55                  60

Asp Glu Ile Val Lys Asp Val Lys Gln Thr Tyr Leu Ala Arg Val
                 65                  70                  75

Phe Ser Tyr Pro Ala Gly Asn Val Glu Ser Thr Gly Ser Ala Gly
                 80                  85                  90

Glu Pro Leu Tyr Glu Asn Ser Pro Glu Phe Thr Pro Tyr Leu Glu
                 95                 100                 105

Thr Asn Leu Gly Gln Pro Thr Ile Gln Ser Phe Glu Gln Val Gly
                110                 115                 120

Thr Lys Val Asn Val Thr Val Glu Asp Asp Gln Thr Ala Val Arg
                125                 130                 135

Arg Asn Asn Thr Asn Leu Ser Leu Arg Asp Val Phe Gly Lys Asp
                140                 145                 150

Leu Ile Tyr Thr Leu Tyr Tyr Trp Lys Ser Ser Ser Ser Gly Ala
                155                 160                 165

Ala Thr Ala Lys Thr Asn Thr Asn Glu Phe Leu Ile Asp Val Asp
                170                 175                 180

Lys Gly Glu Asn Tyr Cys Phe Ser Val Gln Ala Val Ile Pro Ser
                185                 190                 195

Arg Thr Val Asn Arg Lys Ser Thr Asp Ser Pro Val Glu Cys Met
                200                 205                 210

Gly Gln Glu Lys Gly Glu Phe Arg Glu
                215             219
```

-continued

<210> SEQ ID NO 8
<211> LENGTH: 219
<212> TYPE: PRT
<213> ORGANISM: Artificial Sequence
<220> FEATURE:
<221> NAME/KEY: Artificial sequence
<222> LOCATION: 1-219
<223> OTHER INFORMATION: human tissue factor sequence variant

<400> SEQUENCE: 8

```
Ser Gly Thr Thr Asn Thr Val Ala Ala Tyr Asn Leu Thr Trp Lys
  1               5                  10                  15

Ser Thr Asn Phe Lys Thr Ile Leu Glu Trp Glu Pro Lys Pro Val
                 20                  25                  30

Asn Gln Val Tyr Thr Val Gln Ile Ser Thr Lys Ser Gly Asp Trp
                 35                  40                  45

Lys Ser Lys Cys Phe Tyr Thr Thr Ser Thr Glu Cys Asp Leu Thr
                 50                  55                  60

Asp Glu Ile Val Lys Asp Val Lys Gln Thr Tyr Leu Ala Arg Val
                 65                  70                  75

Phe Ser Tyr Pro Ala Gly Asn Val Glu Ser Thr Gly Ser Ala Gly
                 80                  85                  90

Glu Pro Leu Tyr Glu Asn Ser Pro Glu Phe Thr Pro Tyr Leu Glu
                 95                 100                 105

Thr Asn Leu Gly Gln Pro Thr Ile Gln Ser Phe Glu Gln Val Gly
                110                 115                 120

Thr Lys Val Asn Val Thr Val Glu Asp Asp Gln Thr Ala Val Arg
                125                 130                 135

Arg Asn Asn Thr Asn Leu Ser Leu Arg Asp Val Phe Gly Lys Asp
                140                 145                 150

Leu Ile Tyr Thr Leu Tyr Tyr Trp Lys Ser Ser Ser Ser Gly Ala
                155                 160                 165

Ala Thr Ala Lys Thr Asn Thr Asn Glu Phe Leu Ile Asp Val Asp
                170                 175                 180

Lys Gly Glu Asn Tyr Cys Phe Ser Val Gln Ala Val Ile Pro Ser
                185                 190                 195

Arg Thr Val Asn Arg Lys Ser Thr Asp Ser Pro Val Glu Cys Met
                200                 205                 210

Gly Gln Glu Lys Gly Glu Phe Arg Glu
                215             219
```

<210> SEQ ID NO 9
<211> LENGTH: 219
<212> TYPE: PRT
<213> ORGANISM: Artificial Sequence
<220> FEATURE:
<221> NAME/KEY: Artificial sequence
<222> LOCATION: 1-219
<223> OTHER INFORMATION: human tissue factor sequence variant

<400> SEQUENCE: 9

```
Ser Gly Thr Thr Asn Thr Val Ala Ala Tyr Asn Leu Thr Trp Lys
  1               5                  10                  15

Ser Thr Asn Phe Lys Thr Ile Leu Glu Trp Glu Pro Lys Pro Val
                 20                  25                  30

Asn Gln Val Tyr Thr Val Gln Ile Ser Thr Lys Ser Gly Asp Trp
                 35                  40                  45

Lys Ser Lys Cys Phe Tyr Thr Thr Ser Thr Glu Cys Asp Leu Thr
```

-continued

```
                50                  55                  60

Asp Glu Ile Val Lys Asp Val Lys Gln Thr Tyr Leu Ala Arg Val
                65                  70                  75

Phe Ser Tyr Pro Ala Gly Asn Val Glu Ser Thr Gly Ser Ala Gly
                80                  85                  90

Glu Pro Leu Tyr Glu Asn Ser Pro Glu Phe Thr Pro Tyr Leu Glu
                95                  100                 105

Thr Asn Leu Gly Gln Pro Thr Ile Gln Ser Phe Glu Gln Val Gly
                110                 115                 120

Thr Lys Val Asn Val Thr Val Glu Asp Asp Gln Thr Ala Val Arg
                125                 130                 135

Arg Asn Asn Thr Asn Leu Ser Leu Arg Asp Val Phe Gly Lys Asp
                140                 145                 150

Leu Ile Tyr Thr Leu Tyr Tyr Trp Lys Ser Ser Ser Ser Gly Ala
                155                 160                 165

Ala Thr Ala Lys Thr Asn Thr Asn Glu Phe Leu Ile Asp Val Asp
                170                 175                 180

Lys Gly Glu Asn Ala Cys Phe Ser Val Gln Ala Val Ile Pro Ser
                185                 190                 195

Arg Thr Val Asn Arg Lys Ser Thr Asp Ser Pro Val Glu Cys Met
                200                 205                 210

Gly Gln Glu Lys Gly Glu Phe Arg Glu
                215             219


<210> SEQ ID NO 10
<211> LENGTH: 219
<212> TYPE: PRT
<213> ORGANISM: Artificial Sequence
<220> FEATURE:
<221> NAME/KEY: Artificial sequence
<222> LOCATION: 1-219
<223> OTHER INFORMATION: human tissue factor sequence variant

<400> SEQUENCE: 10

Ser Gly Thr Thr Asn Thr Val Ala Ala Tyr Asn Leu Thr Trp Ala
  1               5                  10                  15

Ser Thr Asn Phe Lys Thr Ile Leu Glu Trp Glu Pro Lys Pro Val
                20                  25                  30

Asn Gln Val Tyr Thr Val Gln Ile Ser Thr Lys Ser Gly Asp Trp
                35                  40                  45

Lys Ser Lys Cys Phe Tyr Thr Thr Ser Thr Glu Cys Asp Leu Thr
                50                  55                  60

Asp Glu Ile Val Lys Asp Val Lys Gln Thr Tyr Leu Ala Arg Val
                65                  70                  75

Phe Ser Tyr Pro Ala Gly Asn Val Glu Ser Thr Gly Ser Ala Gly
                80                  85                  90

Glu Pro Leu Tyr Glu Asn Ser Pro Glu Phe Thr Pro Tyr Leu Glu
                95                  100                 105

Thr Asn Leu Gly Gln Pro Thr Ile Gln Ser Phe Glu Gln Val Gly
                110                 115                 120

Thr Lys Val Asn Val Thr Val Glu Asp Asp Gln Thr Ala Val Arg
                125                 130                 135

Arg Asn Asn Thr Asn Leu Ser Leu Arg Asp Val Phe Gly Lys Asp
                140                 145                 150

Leu Ile Tyr Thr Leu Tyr Tyr Trp Lys Ser Ser Ser Ser Gly Ala
                155                 160                 165
```

-continued

```
Ala Thr Ala Lys Thr Asn Thr Asn Glu Phe Leu Ile Asp Val Asp
                170                 175                 180

Lys Gly Glu Asn Ala Cys Phe Ser Val Gln Ala Val Ile Pro Ser
                185                 190                 195

Arg Thr Val Asn Arg Lys Ser Thr Asp Ser Pro Val Glu Cys Met
                200                 205                 210

Gly Gln Glu Lys Gly Glu Phe Arg Glu
                215                 219
```

TISSUE FACTOR PROTEIN VARIANTS

This application claims the benefit of Provisional application Ser. Nos. 60/092,937, filed Jul. 15, 1998, and 60/098,367, filed Aug. 28, 1998.

BACKGROUND OF THE INVENTION

1. Field of the Invention

This invention relates to novel compositions comprising amino acid sequence variants of tissue factor protein. The tissue factor protein variants have a greater affinity for FVII/FVIIa than their mammalian tissue factor protein counterparts. The invention also relates to pharmaceutical compositions comprising the novel compositions as well as their use in diagnostic, therapeutic, and prophylactic methods.

2. Description of Related Disclosures

Tissue factor (TF) is the receptor for coagulation factor VIIa (FVIIa) and the zymogen precursor factor VII (FVII). TF is a 263 amino acid residue glycoprotein composed of a 219 residue extracellular domain, a single transmembrane domain, and a short cytoplasmic domain (Fisher et al., (1987) Thromb. Res. 48:89–99). The TF extracellular domain is composed of two immunoglobulin-like fibronectin type III domains of about 105 amino acids each. Each domain is formed by two anti-parallel β-sheets with Ig superfamily type C2 homology. The protein interaction of FVIIa with TF is mediated entirely by the TF extracellular domain (Muller et al., (1994) Biochem. 33:10864–10870; Gibbs et al., (1994) Biochem. 33:14003–14010; Ruf et al., (1994) Biochem. 33:1565–1572) which has been expressed in *E. coli*, cultured Chinese Hamster Ovary (CHO) cells and *Saccharomyces cerevisiae* (Waxman et al., (1992) Biochemistry 31:3998–4003; Ruf et al., (1991) J. Bio. Chem. 266:2158–2166 and Shigamatsue et al., (1992) J. Biol. Chem. 267:21329–21337). The structures of the human TF (hTF) extracellular domain and its complex with active site inhibited FVIIa have recently been determined by x-ray crystallography (Harlos et al., (1994) Nature 370:662–666; Muller et al., (1994) Biochemistry 33:10864; Banner et al., (1996) Nature 380:41–46).

The hTF extracellular domain has also been extensively characterized by alanine scanning mutagenesis (Kelley et al., (1995) Biochemistry, 34:10383–10392; Gibbs et al., (1994) supra; Ruf et al., (1994) supra). Residues in the area of amino acids 16–26 and 129–147 contribute to the binding of FVIIa as well as the coagulant function of the molecule. Residues Lys20, Trp45, Asp58, Tyr94, and Phe140 make a large contribution (1 kcal/mol) to the free energy (ΔG) of binding to FVIIa (Kelley et al., (1995) supra). Substitution of Lys20 and Asp58 with alanine residues leads to 78- and 30-fold reductions in FVIIa affinity respectively (Kelley et al., (1995) supra). A set of 17 single-site mutants at other nearby sites that are in contact with FVIIa result in modest decreases in affinity ($\Delta\Delta G$=0.3–1.0 kcal $mol^{-1}$). Mutations of TF residues Thr17, Arg131, Leu133 and Val207, each of which contact FVIIa in the crystal structure, have no effect on affinity for FVIIa. Lys15Ala and Tyr185Ala mutations result in small increases in affinity ($\Delta\Delta G$=−0.4 kcal $mol^{-1}$) (Kelley et al., (1995) supra). The 78-fold decrease in affinity imposed by the alanine substitution of Lys20 in hTF can be reversed by substituting a tryptophan for Asp58 (Lee and Kelley, (1998) J. Biol. Chem. 273:4149–4154).

Residues in the area of amino acids 157–168 contribute to the procoagulant function of TF-FVIIa (Kelley et al., (1995) supra; Ruf et al., (1992) J. Biol. Chem. 267:22206–22210) but are not important for FVII/FVIIa binding. It has been shown that lysine residues 165 and 166 are important to TF cofactor function but do not participate in FVIIa complex formation (Roy et al., (1991) J. Biol. Chem. 266:22063; Ruf et al., (1992) J. Biol. Chem. 267:6375). Lysine residues 165 and 166 are located on the C-terminal fibronectin type III domain of TF on the opposite surface of the molecule from residues found to be important for FVIIa binding on the basis of mutagenesis results (Kelley et al., (1995) supra). Alanine substitution of these lysine residues results in a decreased rate of FX activation catalyzed by the TF-FVIIa complex (Ruf et al., (1992) supra). The Lys165Ala-Lys166Ala variant (hTFAA) comprising residues 1–219 of hTF (sTF) inhibits the extrinsic pathway of blood coagulation in vitro through competition with membrane TF for binding to FVIIa. In a rabbit model of arterial thrombosis the variant partially blocks thrombus formation without increasing bleeding tendency (Blood 89, 3219–3227). However, high doses of the variant are required for the antithrombotic effect, in part because FVIIa binds to cell surface TF approximately 1000-fold more tightly than to sTF (Kelley et al. (1997) supra). The greater apparent affinity is due to interaction of the FVIIa γ-carboxyglutamic acid-containing (Gla) domain with phospholipid.

TF is expressed constitutively on cells separated from plasma by the vascular endothelium (Carson, S. D. and J. P. Brozna, (1993) Blood Coag. Fibrinol. 4:281–292). Its expression on endothelial cells and monocytes is induced by exposure to inflammatory cytokines or bacterial lipopolysaccharide (Drake et al., (1989) J. Cell Biol. 109:389). Upon tissue injury, the exposed extracellular domain of TF forms a high affinity, calcium dependent complex with FVII. Once bound to TF, FVII can be activated by peptide bond cleavage to yield serine protease FVIIa. The enzyme that catalyzes this step in vivo has not been elucidated, but in vitro FXa, thrombin, TF-FVIIa and FIXa can catalyze this cleavage (Davie, et al., (1991) Biochem. 30:10363–10370). FVIIa has only weak activity upon its physiological substrates FX and FIX whereas the TF-FVIIa complex rapidly activates FX and FIX.

The TF-FVIIa complex constitutes the primary initiator of the extrinsic pathway of blood coagulation (Carson, S. D. and Brozna, J. P., (1993) Blood Coag. Fibrinol. 4:281–292; Davie, E. W. et al., (1991) Biochemistry 30:10363–10370; Rapaport, S. I. and L. V. M. Rao, (1992) Arterioscler. Thromb. 12:1111–1121). The complex initiates the extrinsic pathway by activation of FX to Factor Xa (FXa), FIX to Factor IXa (FIXa), and additional FVII to FVIIa. The action of TF-FVIIa leads ultimately to the conversion of prothrombin to thrombin, which carries out many biological functions (Badimon, L. et al., (1991) Trends Cardiovasc. Med. 1:261–267). Among the most important functions of thrombin is the conversion of fibrinogen to fibrin, which polymerizes to form a clot. The TF-FVIIa complex also participates as a secondary factor in extending the physiological effects of the contact activation system.

The involvement of this plasma protease system has been suggested to play a significant role in a variety of clinical manifestations including arterial and venous thrombosis, septic shock, adult respiratory distress syndrome (ARDS), disseminated intravascular coagulation (DIC) and various other disease states (Haskel, E. J. et al., (1991) Circulation 84:821–827); Holst, J. et al., (1993) Haemostasis 23 (suppl. 1):112–117; Creasey, A. A. et al., (1993) J. Clin. Invest. 91:2850–2860; see also, Colman R. W. (1989) N. Engl. J. Med 320:1207–1209; Bone, R. C. (1992) Arch. Intern. Med. 152:1381–1389). Overexpression and/or aberrant utilization of TF has been linked to the pathophysiology of both thrombosis and sepsis (Taylor et al., (1991) Circ. Shock 33:127; Warr et al., (1990), Blood 75:1481; Pawashe et al., (1994) Circ. Res. 74:56). TF is expressed on cells found in the atherosclerotic plaque (Wilcox et al., (1989) Proc. Natl. Acad. Sci. U.S.A. 86:2839). Additionally, TF has been implicated in tumor metastasis (Bromberg et al., (1995) Proc. Natl. Acad. Sci., USA, 92:8205). Neutralizing anti-TF monoclonal antibodies have been shown to prevent death in a baboon model of sepsis (Taylor et al., (1991) Circ. Shock 33:127), attenuate endotoxin-induced DIC in rabbits (Warr et al., (1990), Blood 75:1481), and to prevent thrombus reformation in a rabbit model of arterial thrombosis (Pawashe et al., (1994) Circ. Res. 74:56).

SUMMARY OF THE INVENTION

The present invention provides compositions comprising amino acid sequence variants of tissue factor protein. The tissue factor protein variants have a greater affinity for FVII/FVIIa than mammalian tissue factor protein counterparts from which they are derived. In preferred embodiments, the present invention provides compositions which inhibit a TF-FVIIa mediated or associated process such as the catalytic conversion of FVII to FVIIa, FIX to FIXa, or FX to FXa and thereby block initial events of the extrinsic pathway of blood coagulation. Accordingly, the present invention provides tissue factor protein variants that are optionally defective as cofactors for coagulation factor X activation. Therefore, the compositions of the present invention are capable of competing with endogenous tissue factor for binding to FVII or FVIIa and, according to certain aspects, capable of neutralizing the thrombotic effects of endogenous tissue factor.

The compositions of the present invention are useful in therapeutic and prophylactic methods for treating bleeding disorders. For example, according one aspect of the invention the tissue factor protein variant is formulated as a coagulation-inducing therapeutic composition for various chronic and acute bleeding disorders including deficiencies of coagulation factors VIII, IX or XI. According to a further aspect, the invention provides therapeutic and prophylactic methods as well as compositions for inhibiting TF-FVIIa mediated or associated processes. Advantageously, the compositions provide for low dose pharmaceutical formulations.

According to particular aspects of the present invention, a tissue factor protein variant is provided having an amino acid sequence derived from a mammalian tissue factor protein wherein at least one amino acid residue corresponding to a human amino acid residue selected from the group consisting of Asp54, Glu56, Glu130, Arg131, Leu133, Arg135 and Phe140 is substituted with another amino acid, the tissue factor protein variant having a greater affinity for FVII/FVIIa than the mammalian tissue factor protein from which it is derived. Preferably, the tissue factor protein variant is a soluble tissue factor protein variant having at least one amino acid residue selected from the group consisting of Asp54 and Glu56, and at least one amino acid residue selected from the group consisting of Glu130, Arg131, Leu133, Arg135 and Phe140 substituted with another amino acid. According to particular aspects of the invention, the other amino acid residue for Asp54 is preferably selected from the group consisting of Lys, Asn, Glu, Ala and Ser; the other amino acid residue for Glu56 is preferably selected from the group consisting of Asp, His, Gln and Trp; the other amino acid residue for Glu130 is preferably selected from the group consisting of Asp, Ala, Ser and Gly, the other amino acid residue for Arg131is preferably selected from the group consisting of Gln, Ile, Pro, Ser, Leu, Lys, Thr and Met, the other amino acid residue for Leu133 is preferably Ala, the other amino acid residue for Arg135 is preferably selected from the group consisting of Trp, Gln, Leu, Tyr, Thr, and Ala and the other amino acid residue for Phe140 is preferably selected from the group consisting of Asn, His, Val, Ala, Arg and Gly.

The present invention additionally provides for tissue factor protein variants having further amino acid substitutions at amino acid residues which contribute energetically to Factor VII/VIIa binding or which contribute to FVII/FVIIa cofactor activity. Accordingly, the invention provides amino acid sequence variants of tissue factor protein which are defective in FVIIa cofactor function and which have an increased affinity for FVII/FVIIa compared with counterpart tissue factor proteins. According to a particular aspect of the invention at least one additional amino acid residue, preferably selected from the group consisting of Lys15, Asp44, Trp158, Ser163, Gly164, Lys165, Lys166 and Tyr185 is substituted with another amino acid residue such as alanine.

In one embodiment, the composition of the present invention is a polypeptide and the invention encompasses a composition of matter comprising an isolated nucleic acid, preferably DNA, encoding the polypeptide of the invention. According to this aspect, the invention further comprises an expression control sequence operably linked to the DNA molecule, an expression vector, preferably a plasmid, comprising the DNA molecule, where the control sequence is recognized by a host cell transformed with the vector, and a host cell transformed with the vector.

The present invention further extends to therapeutic applications for the compositions described herein. Thus the invention includes a pharmaceutical composition comprising a pharmaceutically acceptable excipient and the composition of the invention. Pharmaceutical compositions comprising these molecules can be used in the treatment or prophylaxis of thrombotic or coagulopathic related diseases or disorders including hereditary deficiencies in coagulation factors, vascular diseases and inflammatory responses. These applications include, for example, a method of treating a mammal for which inhibiting TF-FVIIa is indicated comprising administering a pharmaceutically effective amount of the pharmaceutical composition to the mammal. Such indications include; deep venous thrombosis, arterial thrombosis, post surgical thrombosis, coronary artery bypass graft (CABG), percutaneous transdermal coronary angioplasty (PTCA), stroke, tumor metastasis, inflammation, septic shock, hypotension, ARDS, and DIC. The compositions of the present invention may also be used as an adjunct in thrombolytic therapy.

DETAILED DESCRIPTION OF THE PREFERRED EMBODIMENTS

Definitions

Figure 1:
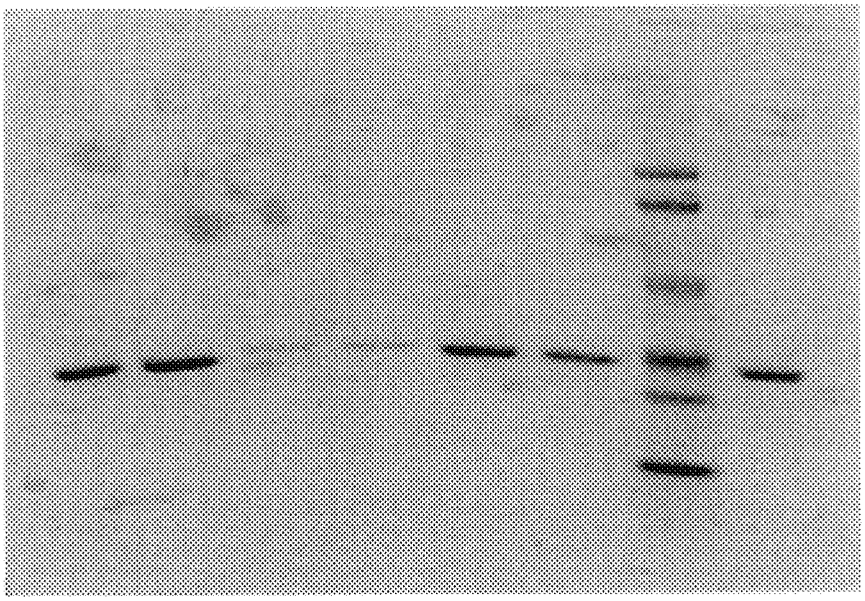
FIG. 1: Human tissue factor proteins having alanine substitutions at residues 165 and 166 (hTFAA) were extracted from *E. coli* cell paste and purified by immunoaffinity chromatography on an anti-TF monoclonal antibody (D3) column (Paborsky, L. R. et al., (1989) Biochemistry 28: 8072–8077) as described for mutants of soluble tissue factor (Kelley, R. F. et al., (1995) Biochemistry 34: 10383–10392). This procedure yielded highly purified sTF protein as shown by SDS-PAGE in FIG. 1. Lane 1-Lys 15Ala-hTFAA, lane 2-Tyr185Ala-hTFAA, lane 3–133cons-hTFAA, lane 4-Asp54Ser-133cons-hTFAA, lane 5-Asp54Ser-133cons-Tyr185Ala-hTFAA, lane 6-Lys15Ala-Asp54Ser-133cons-Tyr185Ala-hTFAA, lane 7-Bio-Rad prestained SDS-PAGE standards, low range, lane 8-hTFAA.

Terms used in the claims and specification are defined as set forth below unless otherwise specified.

Abbreviations used throughout the description include: FIXa for Factor IXa; FXIa for Factor XIa; FXa for Factor Xa; TF for tissue factor; FVII for zymogen factor VII; FVIIa for Factor VIIa; TF-FVIIa for tissue factor-Factor VIIa complex; FVII/FVIIa for FVII and/or FVIIa; sTF for soluble tissue factor composed of the extracellular domain residues 1–219 (SEQ ID NO: 2); hTFAA, the sTF variant containing Lys to Ala substitutions at positions 165 and 166 (SEQ ID NO: 3); TF7I-C for the Kunitz type TF-FVIIa inhibitor of the same name in Dennis et al., (1994) J. Biol. Chem. 269(35): 22129–22136; $K_1$* for apparent equilibrium dissociation constant; PT for prothrombin time; APTT for activated partial thromboplastin time.

The term amino acid or amino acid residue, as used herein, refers to naturally occurring L amino acids or to D amino acids as described further below with respect to variants. The commonly used one- and three-letter abbreviations for amino acids are used herein (Bruce Alberts et al., Molecular Biology of the Cell, Garland Publishing, Inc., New York (3d ed. 1994)).

A TF-FVIIa mediated or associated process or event, or equivalently, an activity associated with plasma FVIIa, according to the present invention is any event which requires the presence of TF-FVIIa. The general mechanism of blood clot formation is reviewed by Ganong, in Review of Medical Physiology, 13th ed., Lange, Los Altos Calif., pp411–414 (1987) and Bach (1988) CRC Crit. Rev. Biochem. 23(4):359–368. Coagulation requires the confluence of two processes, the production of thrombin which induces platelet aggregation and the formation of fibrin which renders the platelet plug stable. The process comprises several stages each requiring the presence of discrete proenzymes and procofactors. The process ends in fibrin crosslinking and thrombus formation. Fibrinogen is converted to fibrin by the action of thrombin. Thrombin, in turn, is formed by the proteolytic cleavage of prothrombin. This proteolysis is effected by FXa which binds to the surface of activated platelets and in the presence of FVa and calcium, cleaves prothrombin. TF-FVIIa is required for the proteolytic activation of FX by the extrinsic pathway of coagulation. Therefore, a process mediated by or associated with TF-FVIIa, or an activity associated with FVIIa includes any step in the coagulation cascade from the formation of the TF-FVII complex to the formation of a fibrin platelet clot and which initially requires the presence TF-FVIIa. For example, the TF-FVIIa complex initiates the extrinsic pathway by activation of FX to FXa, FIX to FIXa, and additional FVII to FVIIa. TF-FVIIa mediated or associated process, or FVIIa activity, can be conveniently measured employing standard assays such as those described in Roy, S., (1991) J. Biol. Chem. 266:4665–4668, and O'Brien, D., et al., (1988) J. Clin. Invest. 82:206–212 for the conversion of Factor X to Factor Xa in the presence of Factor VII and other necessary reagents.

A TF-FVIIa related disease or disorder is meant to include chronic thromboembolic diseases or disorders associated with fibrin formation including vascular disorders such as deep venous thrombosis, arterial thrombosis, stroke, tumor metastasis, thrombolysis, arteriosclerosis and restenosis following angioplasty, acute and chronic indications such as inflammation, septic shock, septicemia, hypotension, adult respiratory distress syndrome (ARDS), disseminated intravascular coagulopathy (DIC) and other diseases. The TF-FVIIa related disorder is not limited to in vivo coagulopathic disorders such as those named above but includes ex vivo TF-FVIIa related processes such as coagulation that may result from the extracorporeal circulation of blood, including blood removed in-line from a patient in such processes as dialysis procedures, blood filtration, or blood bypass during surgery.

"Bleeding disorders" are characterized by a tendency toward hemorrhage, both inherited and acquired. Examples of such bleeding disorders are deficiencies of factors VIII, IX, or XI. Examples of acquired disorders include acquired inhibitors to blood coagulation factors e.g., factor VIII, von Willebrand factor, factors IX, V, XI, XII and XIII, hemostatic disorders as a consequence of liver disease which included decreased synthesis of coagulation factors, bleeding tendency associated with acute and chronic renal disease and hemostasis after trauma or surgery.

The terms "tissue factor protein" and "mammalian tissue factor protein" are used to refer to a polypeptide having an amino acid sequence corresponding to a naturally occurring mammalian tissue factor or a recombinant tissue factor as described below. Naturally occurring TF includes human species as well as other animal species such as rabbit, rat, porcine, non human primate, equine, murine, and ovine tissue factor (see, for example, Hartzell et al., (1989) Mol. Cell. Biol., 9:2567–2573; Andrews et al., (1991) Gene, 98:265–269; and Takayenik et al., (1991) Biochem. Biophys. Res. Comm., 181:1145–1150). The amino acid sequence of the mammalian tissue factor proteins are generally known or obtainable through conventional techniques. In addition to naturally occurring tissue factor proteins the term "mammalian tissue factor protein includes so-called "recombinant" tissue factor proteins which refer to tissue factor proteins in which the nucleic acid sequence encoding the naturally occurring tissue factor protein has been modified to produce a tissue factor protein nucleic acid which encodes the substitution, insertion or deletion of one or more amino acids in the tissue factor protein amino acid sequence. The term further includes "synthetic" tissue factor proteins which are naturally occurring or recombinant tissue factor protein which contain one or more amino acid residues which are not naturally occurring. Suitable modification methods for producing recombinant and synthetic tissue factor proteins are disclosed herein. Synthetic and recombinant tissue factor proteins are generally known in the art and included, for example, sTF (Waxman et al., (1992) Biochemistry 31: 3998–4005) and tissue factor protein mutants which bind functional FVII/FVIIa but have a decreased ability to act as a cofactor for FVII/FVIIa's activation of FX (e.g., hTFAA, see, Lee and Kelley, (1998) J. Biol. Chem. 273:4149–4154). Such tissue factor protein mutants are described in, for example, U.S. Pat. Nos. 5,349,991 and 5,726,147 and are meant to be included within the definition of a mammalian tissue factor protein as described herein.

The TF proteins of the present invention which "correspond to" a mammalian TF are, in general, homologous amino acid sequences of the human, bovine, rat, porcine, canine or other mammalian TF proteins or homologous amino acid sequences of the sequence of SEQ ID NO: 1 including homologous in vitro generated variants having the qualitative biological activity defined herein. Homology with respect to the TF proteins of the present invention is defined as the percentage of amino acid residues in a candidate sequence that are identical with either the amino acid residues in SEQ ID NO: 1, the amino acid sequence of a mammalian TF or a composite sequence as defined herein after aligning the sequences and introducing gaps if necessary to achieve the maximum identity. No N- or C-terminal extension or deletion in the candidate sequence shall be construed as reducing identity. "Composite amino acid" within the present invention refers to an alternate amino acid having the same position in the 263 amino acid residue structure as human TF from other mammalian vertebrate species. Therefore, an amino acid substitution referred to as a composite amino acid substitution replaces the identified amino acid with the equivalent or composite amino acid from another mammalian species. A composite TF sequence is defined as having at least one amino acid from the wild-type sequence replaced with a composite amino acid from another mammalian species.

Therefore, the invention contemplates a TF variant having at least the qualitative biological activity as defined herein and having, for example, at least about 75% amino acid homology with the polypeptide of SEQ ID NO: 1 or the polypeptide of SEQ ID NO: 2. The TF variant amino acid sequence preferably will share at least 80%, more preferably, greater than 85% sequence homology with the sequence of SEQ ID NO: 1 or SEQ ID NO: 2. However, a TF variant or related compound may exhibit less than 50% sequence homology with the sequence of SEQ ID NO: 1 or SEQ ID NO: 2 and still retain the characteristics of a TF variant as described herein.

Included in the definition of TF variant of the present invention are amino acid sequence variants of the SEQ ID NO: 1 or SEQ ID NO: 2 wherein an amino acid in addition to those of the invention has been substituted by another residue, including predetermined mutations (e.g. site directed PCR mutagenesis); other composite amino acid substitutions from other mammalian species of TF such as those listed above and other naturally occurring variants of the foregoing and sequences. Also included is a TF variant as described above wherein the TF variant has been modified by substitution, chemically, enzymatically, or by other appropriate means with a moiety other than a naturally occurring amino acid, it being understood that the variant will have the qualitative biological activity described herein. Exemplary non-naturally occurring amino acid substitution include those described herein below.

As noted, in one embodiment, amino acid substitution variants have at least one amino acid residue in addition to those described herein in the TF variant molecule removed and a different residue inserted in its place. The sites for substitutional mutagenesis include sites where amino acids found in the TF variant from various species are substantially different in terms of side chain bulk, charge and or hydrophobicity. These amino acids are substituted with the exemplary conservative substitutions as described herein below including the exemplary non-naturally occurring amino acids.

Other sites of interest are those in which particular residues of wild-type TF and the variants obtained from various species are identical. These positions may be important for the biological activity of the TF variant. These sites, especially those falling within a sequence of at least three other identically conserved sites, are substituted in a relatively conservative manner. Such conservative substitution are shown below under the heading of preferred conservative substitutions. If such substitutions are shown to preserve qualitative biological activity as defined herein then more substantial changes denominated below as exemplary conservative substitutions may be generated and tested for biological activity.

In this regard, it is understood that amino acids may be substituted on the basis of side chain bulk, charge and/or hydrophobicity. Amino acid residues are classified into four major groups:

Acidic: The residue has a negative charge due to loss of H ion at physiological pH and the residue is attracted by aqueous solution so as to seek the surface positions in the conformation of a peptide in which it is contained when the peptide is in aqueous solution.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/non-polar: The residues are not charged at physiological pH and the residue is repelled by aqueous solution so as to seek the inner positions in the conformation of a peptide in which it is contained when the peptide is in aqueous medium. These residues are also designated "hydrophobic residues."

Neutral/polar: The residues are not charged at physiological pH, but the residue is attracted by aqueous solution so as to seek the outer positions in the conformation of a peptide in which it is contained when the peptide is in aqueous medium.

Amino acid residues can be further classified as cyclic or non-cyclic, aromatic or non aromatic with respect to their side chain groups these designations being commonplace to the skilled artisan.

| Original Residue | Exemplary Conservative Substitution | Preferred Conservative Substitution |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala Phe | Leu |
| Leu | Ile, Val Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |

-continued

| Original Residue | Exemplary Conservative Substitution | Preferred Conservative Substitution |
|---|---|---|
| Val | Ile, Leu, Met, Phe Ala | Leu |

Commonly encountered amino acids which are not encoded by the genetic code, include 2-amino adipic acid (Aad) for Glu and Asp; 2-aminopimelic acid (Apm) for Glu and Asp; 2-aminobutyric (Abu) acid for Met, Leu, and other aliphatic amino acids; 2-aminoheptanoic acid (Ahe) for Met, Leu and other aliphatic amino acids; 2-aminoisobutyric acid (Aib) for Gly; cyclohexylalanine (Cha) for Val, and Leu and Ile; homoarginine (Har) for Arg and Lys; 2,3-diaminopropionic acid (Dpr) for Lys, Arg and His; N-ethylglycine (EtGly) for Gly, Pro, and Ala; N-ethylglycine (EtGly) for Gly, Pro, and Ala; N-ethylasparigine (EtAsn) for Asn, and Gln; Hydroxyllysine (Hyl) for Lys; allohydroxyllysine (AHyl) for Lys; 3-(and 4)hydoxyproline (3Hyp, 4Hyp) for Pro, Ser, and Thr; allo-isoleucine (AIle) for Ile, Leu, and Val; ρ-amidinophenylalanine for Ala; N-methylglycine (MeGly, sarcosine) for Gly, Pro, and Ala; N-methylisoleucine (MeIle) for Ile; Norvaline (Nva) for Met and other aliphatic amino acids; Norleucine (Nle) for Met and other aliphatic amino acids; Ornithine (Orn) for Lys, Arg and His; Citrulline (Cit) and methionine sulfoxide (MSO) for Thr, Asn and Gln; N-methylphenylalanine (MePhe), trimethylphenylalanine, halo (F, Cl, Br, and I)phenylalanine, triflourylphenylalanine, for Phe.

A useful method for identification of certain residues or regions of the TF variant for amino acid substitution other than those described herein for receptor specificity is called alanine scanning mutagenesis as described by Cunningham and Wells (1989) Science, 244:1081–1085. Here a residue or group of target residues are identified (e.g. charged residues such as Arg, Asp, His, Lys, and Glu) and replaced by a neutral or negatively charged amino acid to affect the interaction of the amino acids with the surrounding aqueous environment in or outside the cell. Those domains demonstrating functional sensitivity to the substitution then are refined by introducing further or other variations at or for the sites of substitution. Thus while the site for introducing an amino acid sequence variation is predetermined the nature of the mutation per se need not be predetermined. For example, to optimize the performance of a mutation at a given site, Ala scanning or random mutagenesis may be conducted at the target codon or region and the expressed TF variants screened for the optimal combination of desired activity.

Phage display of protein or peptide libraries offers another methodology for the selection of TF variants with improved affinity, altered specificity, or improved stability (Smith, G. P., (1991) Curr. Opin. Biotechnol. 2:668–673). High affinity proteins, displayed in a monovalent fashion as fusions with the M13 gene III coat protein (Clackson, T., (1994) et al., Trends Biotechnol. 12:173–183), can be identified by cloning and sequencing the corresponding DNA packaged in the phagemid particles after a number of rounds of binding selection.

Other TF variants include fusions such as those described in International Publication No. WO97/20939 as well as C-terminal fusions with proteins having a long half-life such as immunoglobulin constant region or other immunoglobulin regions, albumin, or ferritin as described in WO 89/02922 published Apr. 6, 1989. As used herein, the term "immunoadhesin" designates antibody-like molecules which combine the "binding domain" of a heterologous protein (an "adhesin", e.g. the TF extracellular domain) with the effector functions of immunoglobulin constant domains. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as $IgG_1$, $IgG_2$, $IgG_3$, or $IgG_4$ subtypes, IgA, IgE, IgD or IgM. Immunoadhesins are described in, for example, U.S. Pat. No. 5,116,964.

The sequence of human tissue factor protein (SEQ ID NO: 1) as well as the number given to the amino acids are those described by Fisher et al., (1987) Thrombosis Res. 48:89–99. This residue position number is used in conjunction with the three letter amino acid nomenclature to designate the residue at which a substitution is made in the tissue factor protein variants of this invention. Thus for example, in a tissue factor protein variant in which serine (Ser) replaces aspartic acid (Asp) at residue position number 54 of naturally occurring human tissue factor protein, the nomenclature "Asp54Ser" or the like is used. Multiple substitutions are designated in the same manner with a dash (–) separating each substitution. Thus for example in a tissue factor protein variant which alanine (Ala) residues replace amino acids 15 and 185 of human tissue factor protein the nomenclature "Lys15Ala-Tyr185Ala" is used.

Insofar as the tissue factor protein from mammalian species other than human are used within the context of the present invention, amino acid substitutions made in the sequence of the tissue factor protein other than human are made to the amino acid corresponding to the human amino acid residue after aligning the sequences.

As used herein a "tissue factor protein variant" refers to a tissue factor protein which has an amino acid sequence which is derived from the amino acid sequence of a mammalian tissue factor protein. The amino acid sequence of the tissue factor protein variant is "derived" from the mammalian tissue factor protein amino acid sequence by the substitution of one or more amino acids of the mammalian tissue factor protein according to the invention described herein. Such substitution is generally made by altering the nucleic acid sequence encoding the mammalian tissue factor protein and suitable methods for making such alterations are known in the art and are disclosed herein.

Modes for Carrying Out the Invention

The tissue factor protein variant of the present invention is a mammalian tissue factor protein which, by virtue of, for example, an amino acid substitution in the amino acid sequence of the mammalian tissue factor protein, binds to FVII or FVIIa with sufficient affinity that it effectively competes with a wild-type tissue factor protein when the tissue factor protein variant and the wild-type tissue factor protein are present at physiological concentrations. Preferably the tissue factor protein has an affinity for FVII/FVIIa greater than a wild-type tissue factor protein and more preferably an affinity for FVII/FVIIa greater than the mammalian tissue factor protein from which it was derived. It is therefore a characteristic of the TF variant of the present invention that the protein bind FVII/FVIIa. Accordingly, the TF variant of the present invention shares those residues with a wild-type or mammalian TF protein that are necessary for the binding of TF to FVII/FVIIa. By "bind to FVII/FVIIa" is meant that the TF variant of the present invention has at least the ability to bind to FVII/FVIIa to a degree that TF variant can compete for binding with a wild-type TF at physiological concentrations. Preferred among the TF variants are those that have a KD for FVII/FVIIa of about between 10.0 picomolar (pM) and about 1 micromolar ($\mu$M) in a standard binding assay such as that described by Kelley et al., (1995) supra. More preferably the TF domain has a KD for FVII/FVIIa of about between 10 pM and 10 nanomolar (nM) and most preferably about between 10 pM and 1 nM.

According to the present invention, a tissue factor protein variant is derived from the amino acid sequence of a mammalian tissue factor protein by substitution of at least one amino acid residue corresponding to an amino acid residue of human tissue factor protein selected from the group consisting of Asp54, Glu56, Glu130, Arg131, Leu133, Arg135 and Phe140. Preferably, the tissue factor protein variant has a greater affinity for FVII/FVIIa than the mammalian tissue factor protein from which it is derived. Preferably, the tissue factor protein variant is a soluble tissue factor and preferably a sTF protein variant having at least one amino acid residue selected from the group consisting of Asp54 and Glu56, and at least one amino acid selected from the group consisting of Glu130, Arg131, Leu133, Arg135 and Phe140 substituted with another amino acid.

According to the invention, the other amino acid residue for Asp54 is preferably selected from the group consisting of Asp, Lys, Asn, Glu, Ala and Ser; the other amino acid residue for Glu56 is preferably selected from the group consisting of Asp, His, Gln and Trp; the other amino acid residue for Glu130 is preferably selected from the group consisting of Asp, Ala, Ser and Gly, the other amino acid residue for Arg131is preferably selected from the group consisting of Gln, Ile, Pro, Ser, Leu, Lys, Thr and Met, the other amino acid residue for Leu133 is preferably Ala, the other amino acid residue for Arg135 is preferably selected from the group consisting of Trp, Gln, Leu, Tyr, Thr, and Ala and the other amino acid residue for Phe140 is preferably selected from the group consisting of Asn, His, Val, Ala, Arg and Gly.

Preferably the tissue factor protein variant of the present invention is derived from a mammalian TF protein by substitution of the amino acid residue corresponding to Asp 54 of human TF with Ser, substitution of the amino acid corresponding to Glu 130 with an amino acid selected from the group consisting of Asp, Gly and Ala, substitution of the amino acid residue corresponding to Arg131 with Gln, substitution of the amino acid residue corresponding to Arg135 with an amino acid residue selected from the group consisting of Trp and Gln and substitution of the amino acid corresponding to Phe140 is substituted by Asn.

In a further embodiment the tissue factor protein variant has an affinity for FVII/FVIIa greater than a wild-type tissue factor protein and preferably greater than the mammalian tissue factor protein from which it is derived by substitution of each of amino acid residues corresponding to human amino acid residues Asp54, Glu130, Arg131, Leu133, and Phe140. Preferably the amino acids are substituted according to the scheme provided above.

| wild-type residue | | | | | | |
|---|---|---|---|---|---|---|
| Lys54 | Glu56 | Glu130 | Arg131 | Leu133 | Arg135 | Phe140 |
| residues found in tissue factor protein variants | | | | | | |
| Asp | His | Asp | Gln | Ala | Arg | Asn |
| Asn | Gln | Gly | Ile | | Trp | His |
| Ser | Trp | Ser | Pro | | Gln | Val |
| Ala | | Ala | Ser | | Leu | Ala |
| | | | Leu | | Tyr | Arg |
| | | | Lys | | Thr | Gly |
| | | | Thr | | Ala | |

-continued

| | | | | | | |
|---|---|---|---|---|---|---|
| | | | Met | | | |
| | | | Gln | | | |
| preferred residues found in tissue factor protein variants (where Xaa is any of the foregoing) | | | | | | |
| Xaa | Glu | Asp | Gln | Ala | Xaa | Asn |

The term "133cons" has been used within the context of the present invention to denote a tissue factor variant the sequence Glu130Asp Arg131Gln-Leu133Ala-Arg135Arg-Phe140Asn. Therefore 133cons-hTFAA would denote the hTFAA sequence as defined herein further having the Glu130Asp-Arg131Gln-Leu133Ala-Arg135Arg-Phe140Asn sequence substitutions. Likewise Lys15Ala-133cons-hTFAA denotes the hTFAA sequence as defined herein further having Lys15Ala and Glu130Asp-Arg131Gln-Leu133Ala-Arg135Arg-Phe140Asn substitutions.

According to the present invention, TF variants include but are not limited to full length, phospholipid associated tissue factor proteins having both a transmembrane domain and a cytoplasmic domain as well as TF variants wherein all or a portion of the transmembrane and/or cytoplasmic domain of wild type tissue factor or mammalian tissue factor protein have been deleted. Preferred among the TF variants of the present invention are those TF variants wherein all or a portion of the transmembrane and cytoplasmic domains of wild type tissue factor have been deleted. According to this aspect of the present invention, the TF variant comprises at least a portion of the N-terminal fibronectin type III domain of wild type tissue factor. Preferably, the TF variant comprises at least amino acids 1–102 of wild type tissue factor. More preferably the TF variant of the present invention comprises both fibronectin type III domains of wild type tissue factor. Preferably, according to this aspect of the present invention, at least amino acids 1–219 of wild type TF are present.

The present invention additionally provides for tissue factor protein variants having further amino acid substitutions at amino acid residues which contribute energetically to Factor VII/VIIa binding or which contribute to FVII/FVIIa cofactor activity to provide amino acid sequence variants of tissue factor protein having an increased affinity for FVII/FVIIa compared with counterpart tissue factor proteins which optionally are defective in FVIIa cofactor function. According to this aspect of the present invention at least one additional amino acid residue, preferably selected from the group of amino acids corresponding to human amino acid residues Lys15, Asp44, Trp158, Ser163, Gly164, Lys165, Lys166 and Tyr185 is substituted with another amino acid residue such as alanine.

By way of illustration, substitution, insertion or deletions of particular amino acids along the length of wild type TF produce TF variants with reduced ability to act as a cofactor for FVIIa. The skilled artisan will recognize those residues of wild type TF which contribute to the procoagulant function of TF. For example, residues in the area of amino acids 157–168 contribute to the procoagulant function of TF-FVIIa (Kelley et al., (1995) supra; Ruf et al., (1992) supra) but are not important for FVII/FVIIa binding. According to the present invention any or all of these amino acids are selectively substituted or deleted to provide a TF domain that binds to FVII/FVIIa but is capable of neutralizing the procoagulant activity of wild type tissue factor.

In a preferred embodiment, any or all of residues Trp158, Lys159, Ser163, Gly164, Lys165, Lys166, and Tyr185 of wild type tissue factor are selectively substituted or deleted to provide a TF domain of the present invention. Preferred substitutions are described in U.S. Pat. No. 5,346,991 and include substitution with an amino acid other than one bearing a substantially positively charged side chain at physiological pH. Exemplary substitutions include any or all of Trp158Phe, Lys159Ala, Ser163Ala, Lys165Ala, Lys166Ala, and Tyr185Ala. In a most preferred aspect of the present invention, lysine residues 165 and 166 which are important to TF cofactor function but do not interfere with FVIIa complex formation (Roy et al., (1991) J. Biol. Chem. 266:22063; Ruf et al., (1992) J. Biol. Chem. 267:6375) are selectively substituted. Therefore, according to a preferred aspect of the present invention at least residues 165 and 166 of wild type tissue factor are selectively substituted to result in a molecule which retains its ability to bind FVII/FVIIa but has a reduced ability to act as a cofactor as described. In a particular aspect, alanine substitution of these residues is preferred although any substitution which results in a decreased rate of FX activation catalyzed by the TF-FVIIa complex (Ruf et al., (1992) supra) is appropriate.

Preferred tissue factor variants of the present invention are those described in U.S. Pat. No. 5,346,991, entitled "Tissue Factor Mutants Useful for the Treatment of Myocardial Infarction and Coagulopathic Disorders" the disclosure of which is specifically incorporated herein by reference. This patent describes the generation of tissue factor variants that are capable of inhibiting the ability of endogenous tissue factor to induce coagulation. These variants have either or both of the positively charged amino acid residues 165 and 166 substituted with an α-amino acid other than one bearing a substantially positively charged side chain at physiological pH. The variants include human tissue factor molecules as described above having the cytoplasmic portion of wild type tissue factor, residues 244–263, removed, as well as the transmembrane region at residues 220–243. Any of the tissue factor variants may appropriately form the TF domain of the present invention. International Publication No. WO 94/28017 also describes TF variants that are able to bind FVII/FVIIa and have a reduced procoagulant cofactor activity. Most preferred among the molecules described therein are a tissue factor protein having an amino acid sequence homologous to a wild type tissue factor protein and wherein at least one amino acid associated with TF cofactor function is selectively substituted, deleted or replaced to result in a molecule which retains its ability to bind FVII/FVIIa but which has reduced ability to act as a cofactor as described above.

The skilled artisan will recognize other amino acid residues in TF that contribute to the FVIIa binding (Kelley et al. (1995) supra; Gibbs et al., (1994) supra; Ruf et al., (1994) Biochemistry, 33, 1565–1572; Schullek et al., (1994) J. Biol. Chem. 269:19399–19403; Muller et al., (1994) 33:10864–10869). According to the present invention, the TF variants share at least those residues with wild type TF which are required for FVIIa/FVII binding, as described. Preferably, the tissue factor variant will share at least about 80% sequence homology and more preferably between about 85%–95% sequence homology with wild-type tissue factor protein.

Various techniques are available which may be employed to produce DNA, which can encode proteins for the recombinant synthesis of the tissue factor variants of the invention. For instance, it is possible to derive DNA based on naturally occurring DNA sequences that encode for changes in an amino acid sequence of the resultant protein. These mutant DNA can be used to obtain the tissue factor variants of the present invention. These techniques contemplate, in simplified form, obtaining a gene encoding a tissue factor modifying the genes by recombinant techniques such as those discussed below; inserting the genes into an appropriate expression vector; inserting the vector into an appropriate host cell; culturing the host cell to cause expression of the hybrid molecule; and purifying the molecule produced thereby.

Somewhat more particularly, a DNA sequence encoding the tissue factor variant of the present invention is obtained by synthetic construction of the DNA sequence (Sambrook, J. et al., Molecular Cloning (2nd ed.), Cold Spring Harbor Laboratory, N.Y., (1989).

By way of example, expression vectors encoding wild type tissue factor can be obtained and subject to site specific mutagenesis (Kunkel et al., (1991) Methods Enzymol. 204:125–139; Carter, P., et al., (1986) Nucl. Acids. Res. 13:4331; Zoller, M. J. et al., (1982) Nucl. Acids Res. 10:6487), cassette mutagenesis (Wells, J. A., et al., (1985) Gene 34:315), or restriction selection mutagenesis (Wells, J. A., et al., (1986) Philos. Trans, R. Soc. London Ser A 317, 415) to obtain the tissue factor domain of the molecule. The mutant DNA can then be used by insertion into expression vectors containing DNA encoding an active site inhibitor domain.

Oligonucleotide-mediated mutagenesis is a preferred method for preparing the DNA encoding the tissue factor variants of the present invention. This technique is well known in the art as described by Adelman et al., (1983) DNA, 2:183. Briefly, the native or unaltered DNA of a wild type tissue factor is altered by hybridizing an oligonucleotide encoding the desired mutation to a DNA template, where the template is the single-stranded form of a plasmid or bacteriophage containing the unaltered or native DNA sequence.

The DNA encoding variants are then inserted into an appropriate plasmid or vector. The vector is used to transform a host cell. In general, plasmid vectors containing replication and control sequences which are derived from species compatible with the host cell are used in connection with those hosts. The vector ordinarily carries a replication site, as well as sequences which encode proteins that are capable of providing phenotypic selection in transformed cells.

For example, *E. coli* may be transformed using pBR322, a plasmid derived from an *E. coli* species (Mandel, M. et al., (1970) J. Mol. Biol. 53:154). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-lambda represent expression vectors with the tac, trp, or $P_L$ promoters that are currently available (Pharmacia Biotechnology).

Other preferred vectors can be constructed using standard techniques by combining the relevant traits of the vectors described herein. Relevant traits of the vector include the promoter, the ribosome binding site, the variant gene or gene fusion, the signal sequence, the antibiotic resistance markers, the copy number, and the appropriate origins of replication.

The host cell may be prokaryotic or eukaryotic. Prokaryotes are preferred for cloning and expressing DNA sequences to produce parent polypeptides, segment substituted polypeptides, residue-substituted polypeptides and polypeptide variants. For example, *E. coli* K12 strain 294 (ATCC No. 31446) may be used as *E. coli* B, *E. coli* X1776

(ATCC No. 31537), and *E. coli* c600 and c600hfl, *E. coli* W3110 (F-, gamma-, prototrophic /ATCC No. 27325), bacilli such as *Bacillus subtilis*, and other enterobacteriaceae such as *Salmonella-typhimurium* or *Serratia marcesans*, and various pseudomonas species. The preferred prokaryote is *E. coli* W3110 (ATCC 27325). When expressed by prokaryotes the polypeptides typically contain an N-terminal methionine or a formyl methionine and are not glycosylated. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure (Tissue Culture, Academic Press, Kruse and Patterson, eds. [1973]). Examples of such useful host cell lines are VERO and HeLa cells, Chinese Hamster Ovary (CHO) cell lines, W138, 293, BHK, COS-7 and MDCK cell lines.

2. Compositions

The tissue factor protein variants of the present invention is typically provided in a compositional form that is suitable for its intended use. The variant of the present invention can be prepared in the soluble form such as the hTFAA form described herein.

The tissue factor variant of the present invention may also comprise all or a portion of the transmembrane domain of wild type tissue factor. It is preferred, according to the present invention, a TF variant containing a membrane anchor domain be formulated in a composition comprising a mild detergent or phospholipid (PL). Although the composition of the present invention comprising a full-length TF domain including a membrane anchor or transmembrane domain retain their biological activity they are preferably formulated in a phospholipid composition. International Publication No. WO 94/28017 describes the preparation of phospholipid compositions comprising a TF domain that are appropriate for the compositions of the present invention.

Preferred compositions described in WO 94/28017 and suitable for the pharmaceutical compositions of the present invention are phospholipid compositions which afford maximum stability and biological activity for the composition. Such phospholipid compositions are preferably formulated to form liposome compositions, as are generally well known in the art. As described, suitable phospholipids for use in the liposome compositions of the present invention include those which contain fatty acids having twelve to twenty carbon atoms; said fatty acids may be either saturated or unsaturated. Preferred phospholipids for use according to the present invention include phosphatidylcholine (PC), phosphatidylethanolamine (PE), phosphatidylglycerol (PG) and phosphatidylserine (PS). These phospholipids may come from any natural source and the phospholipids, as such, may be comprised of molecules with differing fatty acids. Phospholipid mixtures comprising phospholipids from different sources may be used. For example, PC, PG and PE may be obtained from egg yolk; PS may be obtained from animal brain and spinal chord. These phospholipids may come from synthetic sources as well. The phospholipids are conveniently combined in the appropriate ratios to provide the phospholipid mixture for use in preparing the composition of the present invention.

The preparation of liposomes is generally well known and has been previously described. Exemplary methods for preparation of liposomes includes reverse loading of liposomes (see U.S. Pat. No. 5,104,661), or in the manner described for the incorporation of amphotericin B into lipid vesicles. (See, e.g., Lopez-Berenstein et al., (1985) J. Infect. Dis., 151:704–710; Lopez-Berenstein, (1987) Antimicrob. Agents Chemother., 31:675–678; Lopez-Berenstein et al., (1984) J. Infect. Dis., 150:278–283; and Mehta et al., (1984) Biochem. Biophys. Acta, 770:230–234). Liposomes with enhanced circulation time may also be prepared as described in U.S. Pat. No. 5,013,556.

Thus, in one embodiment, the present invention contemplates the preparation of the tissue factor variants in the form of liposomes having TF portion of the molecule associated with the lipid bilayer of the liposomes, such that the TF membrane anchor domain is inserted through the lipid bilayer.

Other suitable compositions of the present invention comprise any of the above noted compositions with a pharmaceutically acceptable carrier, the nature of the carrier differing with the mode of administration, for example, in oral administration, usually using a solid carrier and in I.V. administration, a liquid salt solution carrier.

The compositions of the present invention include pharmaceutically acceptable components that are compatible with the subject and the protein of the invention. These generally include suspensions, solutions and elixirs, and most especially biological buffers, such as phosphate buffered saline, saline, Dulbecco's Media, and the like. Aerosols may also be used, or carriers such as starches, sugars, microcrystalline cellulose, diluents, granulating agents, lubricants, binders, disintegrating agents, and the like (in the case of oral solid preparations, such as powders, capsules, and tablets).

As used herein, the term "pharmaceutically acceptable" generally means approved by a regulatory agency of the Federal or a state government or listed in the U.S. Pharmacopeia or other generally recognized pharmacopeia for use in animals, and more particularly in humans.

The formulation of choice can be accomplished using a variety of the aforementioned buffers, or even excipients including, for example, pharmaceutical grades of mannitol, lactose, starch, magnesium stearate, sodium saccharin cellulose, magnesium carbonate, and the like. "PEGylation" of the compositions may be achieved using techniques known to the art (see for example International Patent Publication No. WO92/16555, U.S. Pat. No. 5,122,614 to Enzon, and International Patent Publication No. WO92/00748). Oral compositions may be taken in the form of solutions, suspensions, tablets, pills, capsules, sustained release formulations, or powders.

3. Therapeutic methods

The molecules of the present invention can be used therapeutically to induce coagulation or conversely, where the tissue factor variant is defective as a cofactor for activation of FX, to prevent the biological activity of the TF-FVIIa complex. The inhibition of TF-FVIIa is desirable in indications where the reduction of TF-FVIIa dependent coagulation is implicated. These situations include but are not limited to the prevention of arterial re-thrombosis in combination with thrombolytic therapy. It has been suggested that the TF-FVIIa plays a significant role in a variety of clinical states including deep venous thrombosis, arterial thrombosis, stroke, DIC, septic shock, cardiopulmonary bypass surgery, adult respiratory distress syndrome, hereditary angioedema. Inhibitors of TF-FVIIa may therefore play important roles in the regulation of inflammatory and/or thrombotic disorders.

Thus the present invention encompass a method for preventing TF-FVIIa mediated event in a human comprising administering to a patient in need thereof a therapeutically effective amount of the tissue factor variant of the present invention. A therapeutically effective amount of the hybrid molecule of the present invention is predetermined to achieve the desired effect. The amount to be employed therapeutically will vary depending upon therapeutic objectives, the routes of administration and the condition being treated. Accordingly, the dosages to be administered are sufficient to bind to available FVII/FVIIa and form an inactive complex leading to decreased coagulation in the subject being treated.

The therapeutic effectiveness is measured by an improvement in one or more symptoms associated with the TF-FVIIa dependent coagulation. Such therapeutically effective dosages can be determined by the skilled artisan and will vary depending upon the age condition, sex and condition of the subject being treated. Suitable dosage ranges for systemic administration are typically between about 1 $\mu$g/kg to up to 100 mg/kg or more and depend upon the route of administration. According to the present invention a preferred therapeutic dosage is between about 1 $\mu$g/kg body weight and about 5 mg/kg body weight. For example, suitable regimens include intravenous injection or infusion sufficient to maintain concentration in the blood in the ranges specified for the therapy contemplated.

Pharmaceutical compositions which comprise the polypeptides of the invention may be administered in any suitable manner, including parental, topical, oral, or local (such as aerosol or transdermal) or any combination thereof. Suitable regimens also include an initial administration by intravenous bolus injection followed by repeated doses at one or more intervals.

Where the composition of the invention is being administered in combination with a thrombolytic agent, for example, for the prevention of reformation of an occluding thrombus in the course of thrombolytic therapy, a therapeutically effective dosage of the thrombolytic is between about 80 and 100% of the conventional dosage range. The conventional dosage range of a thrombolytic agent is the daily dosage used in therapy and is readily available to the treating physician. (Physicians Desk Reference 1994, 50th Edition, Edward R. Barnhart, publisher). The typical dosage range will depend upon the thrombolytic being employed and include for tissue plasminogen activator (t-PA), 0.5 to about 5 mg/kg body weight; streptokinase, 140,000 to 2,500,0000 units per patient; urokinase, 500,000 to 6,250,00 units per patient; and anisolated streptokinase plasminogen activator complex (ASPAC), 0.1 to about 10 units/ kg body weight.

The term combination as used herein includes a single dosage form containing at least the molecule of the present invention and at least one thrombolytic agent. The term is also meant to include multiple dosage forms wherein the molecule of the present invention is administered separately but concurrently by two separate administration, such as in sequential administration. These combinations and compositions work to dissolve or prevent the formation of an occluding thrombus resulting in dissolution of the occluding thrombus.

According to a further aspect of the invention the molecule may be employed in preventing ex vivo coagulation such as that encountered in the extracorporeal perfusion of blood through for example artificial valves, prothesis, stents or catheters. According to this aspect of the invention the extracorporeal devise may be coated with the compositions of the invention resulting a lower risk of clot formation due to extrinsic pathway activation.

The following examples are offered by way of illustration and not by way of limitation. The disclosures of all citations in the specification are expressly incorporated herein by reference.

EXAMPLES

Materials

Human Factor VIIa, Factor X, Factor Xa, as well as biotinylated glutamyl-glycyl-arginine chloromethyl ketone (BEGR-CK) were purchased from Haematologic Technologies Inc. (Essex Jct., VT). Chromogenic substrates Chromozym t-PA (N-methylsulfonyl-D-phenyl-L-glycyl-L-arginine-p-nitroanilide acetate) and Spectrozyme FXa (methoxycarbonyl-D-cyclohexylglycyl-L-glycyl-L-arginine-p-nitroanilide acetate) were from Boehringer Mannheim and American Diagnostica, respectively. Substrates S-2266 (D-valyl-L-leucyl-L-arginine-p-nitroanilide dihydrochloride), S-2288 (H-D-isoleucyl-L-prolyl-L-arginine-p-nitroanilide dihydrochloride), and S-2366 (L-pyroglutamyl-L-prolyl-L-arginine-p-nitroanilide hydrochloride) were from Pharmacia Hepar. Substrate S-2765 (N-a-Benzyloxycarbonyl-D-arginyl-L-glycyl-L-arginin-p-nitroanilide hydrochloride) was purchased from Chromogenix. Membrane tissue factor (mTF) was prepared by sonication of a human embryonic kidney cell line (293) expressing recombinant, full length (residues 1–263) human TF (Paborsky, L. R. et al., Protein Engineering 3: 547–553 [1990]). TF(1–243) is TF lacking the cytoplasmic domain that was constructed, purified and formulated in detergent as previously described (Paborsky,(1989) Biochemistry 28:8072). TF(1–243) was relipidated with a 70/30 mixture of phosphatidyl choline/phosphatidyl serine by using the detergent dialysis procedure of Mimms et al. (1981) Biochemistry 20:833 as modified by Bach et al. (1986) Biochemistry 25:4007–4020. Bovine trypsin, 4-methylumbelliferyl p-guanidinobenzoate and CHAPS were purchased from Sigma Chemicals, Inc. Bovine serum albumin (BSA), Fraction V was obtained from Calbiochem (La Jolla, Calif.). $N^{\alpha}$-Benzoyl-L-arginine-p-nitroanilide was purchased from Bachem California (Torrance, Calif.). Human thromboplastin (Innovin) was purchased from Dade International, Inc. (Miami, Fla.). All other reagents were of the highest grade commercially available.

Example 1

Construction and Sorting of sTF Phage Libraries

Phagemids encoding sTF fused to the carboxyl-terminal domain (residues 249–406) of the M13 gene III product were constructed using standard molecular biology techniques (Sambrook et al., (1989) "Molecular Cloning: A laboratory manual," Cold Spring Horbor Laboratory, Cold Spring Harbor, N.Y.) from a vector, phGH-g3, previously developed for monovalent phage display (Lowman, H.B. et al., (1991) Biochemistry 30: 10832; Lowman and Wells (1991) Methods in Enz., 3:205). These phagemids have an amber stop codon at the end of the sTF sequence such that the sTF-gene III fusion protein is produced when expressed in an *E. coli* strain, such as XL-1 Blue (Stratagene), that is functional for suppression of amber stop codons. Upon expression in a non-suppressor strain, such as 33B6, only sTF is produced. Expression is under control of the alkaline phosphatase promoter and the stII signal sequence is used to effect secretion of the gene product. One phagemid, called pTFAA-g3, encodes the sTF variant containing Lys to Ala substitutions at positions 165 and 166, and was used as the starting template for construction of library 1. A second phagemid, pTF-g3, encodes wild-type sTF and was used in the construction of library 2.

In preparation for library 1 construction, oligonucleotide-directed, site-specific mutagenesis (Kunkel (1985) Proc. Natl. Acad. Sci. USA 82:488) was performed on phagemid pTFAA-g3 to create DNA templates that encode TFAA variants with markedly lower affinity for FVIIa. This strategy ensured that phage incorporating TF encoded from the template DNA would be less likely to compete with library-derived phage for FVIIa binding should the mutagenic efficiency be sub-optimal. Specifically, for library 1 the template phagemid encoded a Lys to Ala substitution at residue 20 (K20A) and an Asp to Glu substitution at position 58 (D58E), in addition to the Lys to Ala substitutions at positions 165 and 166. Mutant libraries were then created by substituting five TF codons simultaneously with NNS nucleotide sequences (where N=G/A/T/C; S=G/C) via oligonucleotide-directed mutagenesis of the altered pTFAA-g3 template. For library 2, the starting template was pTF-g3 with a TAA stop codon replacing Leu133. This strategy ensured that clones arising from the unmutated template sequence would not express sTF-g3 fusion proteins. For construction of library 1, two primers were used to simultaneously mutate codons at positions 20 and 21, and at positions 54, 56 and 58, respectively, in the pTFAA (K20A, D58E)-g3 template. Library 2 used pTF (133stop)-g3 as template with randomization of codons 130, 131, 133, 135 and 140 by using a single oligonucleotide primer. The preparation of filamentous phage displaying sTF variants, by electroporation of phagemid libraries into *E. coli* strain XL1-Blue (Stratagene), and subsequent infection of bacteria with helper phage VCS M13 (Stratagene), was performed as described (Lowman and Wells (1991) supra). At least 10 clones from each of the unselected libraries were sequenced in order to ascertain the mutagenic efficiency. Library 1 contained $1\times10^8$ transformants with about 10% of the clones having both sites mutated. Library 2 had $7.5\times10^8$ transformants with a 60% mutation frequency.

Binding Enrichments. Phage particles displaying sTF variants were sorted on the basis of binding to biotinylated FVIIa (BEGR-7a). BEGR-7a was prepared using a biotinylated tripeptide chloromethyl ketone (BEGR-CK) active site inhibitor as described elsewhere (Kelley et al., (1995) Biochem. 34:10383–10392). Microtiter plate wells coated with streptavidin (Molecular Probes) and blocked with milk proteins were used to capture BEGR-7a. For selection experiments phage displaying libraries of TF variants, in buffer containing 20 mM Tris, pH 7.5, 100 mM NaCl, 5 mM $CaCl_2$ (TNC), were incubated in wells containing either streptavidin+BEGR-7a or streptavidin alone. After 1–2 hr incubation at ambient temperature, unbound phage were removed and the wells washed extensively with TNC buffer containing 0.05% Tween-20. Bound phage were then eluted using 50 mM EDTA in a 10 min incubation at 37° C. The titer of infective TF-containing phage particles eluted from the wells was determined by infecting XL-1 Blue cells with eluted phage, streaking dilutions to LB plates containing ampicillin (to select for cells bearing TF-encoding phagemids), and counting colony-forming units (CFU). The ratio of the phage titer (CFU/mL elution buffer) from wells containing FVIIa to the titer eluted from wells containing streptavidin alone was calculated to monitor per-round enrichments in specific binding.

Both libraries 1 and 2 gave significant enrichment for specific binding to FVIIa as shown in Tables I and II below. After 4 rounds of sorting, 12 selectants from library 1 were subjected to DNA sequencing providing the amino acid sequences at the library positions shown in Table I. The consensus sequence obtained from this library was nearly identical with the wild-type sequence except for variation at residue 54. These selectants were expressed in *E. coli* 27C7, a non-suppressor strain, the sTF proteins were purified by immunoaffinity chromatography and the dissociation constant (Kd) for FVIIa binding determined as described previously (Kelley, R. F. et al., Biochemistry 34: 10383–10392 [1995]). Clones with either Ser or Asn replacing Asp54 gave about a 2-fold higher affinity for binding to FVIIa.

TABLE I

Identity of hTFAA variants selected on the basis of binding immobilized BEGR7a.
Library 1, after 4 rounds of sorting:

| | Residue position | | | | | | $K_D$ (hTFAA) ‡ |
|---|---|---|---|---|---|---|---|
| | 20 | 21 | 54 | 56 | 58 | | $K_D$ (mut) |
| hTFAA | K | T | D | E | D | | 1 |
| Selectants | K | T | K | E | D | (2) | 1.4 |
| | K | T | N | E | D | | 1.8 |
| | K | T | E | H | D | (3) | 1.0 |
| | K | T | S | E | D | | 2.3 |
| | K | T | D | Q | D | | 0.9 |
| | K | T | A | E | D | (3) | 1.1 |
| | K | T | D | W | D | | 0.9 |
| Consensus | K | T | var¶ | E | D | | ND |

Numbers in parentheses indicate the number of times the given variant appeared amongst the selected clones. The consensus sequence reflects those residues selected at each position which were significantly enriched (≧4 – fold) above their expected random frequency in an NNS-based library (Lowman and Wells (1993) J. Mol. Biol. 234:564). ‡ Dissociation constants for hTFAA and its variants were determined from kinetic parameters for binding immobilized FVIIa using a BIAcore instrument. ND = not determined. This position was quite variable, with no strong consensus observed.

DNA sequences were determined for selectants from library 2 after 7 rounds of sorting with the amino acid sequences given in Table II. The amino acid sequences obtained from sorting of library 2 were more diverse than library 1 and were quite different from the wild-type sequence. Positions 131 and 135 were quite variable and the wild-type residue was not observed at 131. Residue 140, which is a Phe in wild-type sTF, contacts FVIIa in the co-crystal, and was shown to be important for binding by alanine-scanning mutagenesis, gave a consensus Asn. All of the clones had Ala in place of Leu133, a residue that contacts FVIIa in the co-crystal. A consensus sequence of Asp130, Gln131, Ala1 33, Arg135, Asn140 was determined from sorting of library 2.

TABLE II

Distribution of residues at randomized positions in 10 clones after 7 rounds of sorting. (Numbers in parentheses indicate the number of times a given residue appeared at that position in the primary sequence. The consensus sequence reflects those residues selected at each position that were significantly enriched above their expected random frequency in an NNS-based library.)

| | Residue Position | | | | |
|---|---|---|---|---|---|
| | 130 | 131 | 133 | 135 | 140 |
| Wild-type | Glu | Arg | Leu | Arg | Phe |
| Template | Glu | Arg | STOP | Arg | Phe |
| Residues | Asp (5) | Gln (3) | Ala (10) | Arg (2) | Asn (5) |
| Found in | Gly (2) | Ile | | Trp (2) | His |
| Clones | Ala (2) | Pro | | Gln (2) | Val |
| | Ser | Ser | | Leu | Ala |
| | | Leu | | Tyr | Arg |
| | | Lys | | Thr | Gly |
| | | Thr | | Ala | |
| | | Met | | | |
| Consensus | Asp | Gln | Ala | Var[a] | Asn |

[a]This position was quite variable, with no strong consensus observed.

Example 2

Production and Characterization of hTFAA Variants

In order to further compare binding affinities for FVIIa, and to construct an hTFAA variant with higher anticoagulant potency, variants were produced in the Lys165Ala:Lys166Ala mutant sTF by oligonucleotide-directed mutagenesis of pTFAA-g3. Variants constructed included single-site mutants of Lys15Ala, Ser54Ala, and Tyr185Ala, as well as the library 2 consensus sequence Asp130-Gln131-Ala133-Arg135-Asn140. Mutants having one or more of the Lys15Ala, Ser54Ala, Tyr185Ala substitutions combined with the library 2 consensus sequence were also prepared. Phagemids were transformed into *E. coli* strain 33B6, a non-suppressor strain that is a derivative of *E. coli* W3110, for expression. Overnight saturated cultures were used to inoculate (1%) 10 L of media in a fermentation tank. Fermentation was performed as described previously (Carter, P. et al., Bio/Technology 10: 163–167 [1992]) except that the temperature was 30° C. rather than 37° C. hTFAA proteins were secreted into the periplasm by virtue of the stII signal sequence. Cells were harvested by centrifugation 32 hours after inoculation and stored frozen at −20° C.

hTFAA proteins were extracted from *E. coli* cell paste and purified by immunoaffinity chromatography on an anti-TF monoclonal antibody (D3) column (Paborsky, L. R. et al., Biochemistry 28: 8072–8077 [1989]) as described for mutants of soluble tissue factor (Kelley, R. F. et al., Biochemistry 34: 10383–10392 [1995]). This procedure yielded highly purified sTF protein as shown by SDS-PAGE in FIG. 1. Concentrations of the purified sTF proteins were determined by: 1) Detection with the D3 antibody (Lee, G. F. et al., Biochemistry 36: 5607–5611 [1997]), and 2) absorbance measurements.

TABLE III hTFAA Variants

| Variant | SEQ ID NO: |
|---|---|
| hTFAA | 3 |
| Lys15Ala-hTFAA | 4 |
| Asp54Ser-hTFAA | 5 |
| Tyr185Ala-hTFAA | 6 |
| 133cons-hTFAA | 7 |
| Asp54Ser-133cons-hTFAA | 8 |
| Asp54Ser-133cons-Tyr185Ala-hTFAA | 9 |
| Lys15Ala-Asp54Ser-133cons-Tyr185Ala-hTFAA | 10 |

Example 3

Determination of Equilibrium Dissociation Constants for Inhibition of TF-FVIIa-dependent Factor X Activation by hTFAA Variants The relative potency of the hTFAA variants for inhibiting the catalytic function of the mTF·FVIIa complex was evaluated by using an assay of factor X activation. In this assay, FX is added to a solution of mTF·FVIIa and the rate of FXa formation is determined by removing aliqouts at various times, quenching the reaction by addition of EDTA to chelate calcium, and then measuring the amount of FXa formed by using a FXa specific substrate, either Spectrozyme FXa or S-2765. FXa cleavage of these substrates does not require calcium; hydrolysis is monitored by absorbance measurements at 405 nM. The rate may be used to calculate the FXa concentration by reference to a standard curve constructed with purified FXa. FX activation assays were conducted in a microtiter format and absorbance changes were monitored on an SLT EAR340AT plate reader controlled by a Macintosh SE computer equipped with Biometallics DeltaSoftII software. Nonlinear regression analysis was carried out using KaleidaGraph v3.01 (Synergy Software). The concentration of a stock solution of FVIIa was determined by active site titration with a quantitated sample of TF7I-C and by using Chromozym t-PA as the substrate for FVIIa. The concentration of TF7I-C had been accurately determined by titration with trypsin that had been active site-titrated using 4-methylumbelliferyl p-guanidinobenzoate (Jameson, G. W. et al., (1973) Biochem. J. 131:107–117). After a 1 h incubation of 80 nM trypsin plus an aliquot of diluted inhibitor in 50 mM Tris, pH 8.0, 100 mM NaCl, 10 mM $CaCl_2$, and 0.05% Triton X-100 at room temperature, 20 $\mu$l of 5 mM $N^\alpha$-benzoyl-L-arginine-p-nitroanilide was added to a total volume of 150 $\mu$l. The change in absorbance at 405 nm was then monitored. The concentrations determined assumed a 1:1 stoichiometry of inhibitor with trypsin or FVIIa. The concentration of mTF was then determined from the increase in the rate of Chromozym t-PA hydrolysis upon addition to a solution of the active site quantitated FVIIa. The concentration of FX and FXa was that supplied by the manufacturer.

In most cases, the equilibrium inhibition constants for hTFAA variants were determined in assays employing 100 pM mTF·FVIIa and chromogenic substrate Spectrozyme FXa. These assays used a buffer solution of 20 mM HEPES pH 7.4, 150 mM NaCl, 0.1% PEG-8000, and 5 mM $CaCl_2$. The substrate FX concentration was 200 nM and the total volume of the reaction mixture was 200 $\mu$L. In tests of the inhibitory properties of the hTFAA variants, FVIIa was incubated with FX and a varied concentration of the hTFAA variant for 30 minutes at 37° C. prior to addition of mTF. After adding mTF, incubation at 37° C. was continued and 25 $\mu$L aliqouts of the reaction mixture were removed at 1, 2, 3, 4, 5, 7.5, and 10 minutes after mTF addition and mixed with an equal volume of 50 mM EDTA to quench activation of FX. The amount of FXa formed was measured by adding Factor Xa buffer (10X=0.2 M HEPES pH 7.4, 1.5 M NaCl, 0.25 M EDTA, 1% PEG-8000) to a final concentration of 1X followed by 0.5 mM Spectrozyme FXa. The final volume for each time point was 200 $\mu$L and the rates of Spectrozyme FXa hydrolysis were monitored by changes in the absorbance at 405 nm at ambient temperature and are reported in mOD/min.

A more sensitive assay was required to examine inhibition by the more potent hTFAA variants. These assays employed 25 pM mTF·FVIIa and used substrate S-2765 to quantitate FXa formation. The reaction buffer was 20 mM EPPS pH 8.2, 100 mM NaCl, 5 mM $CaCl_2$, 0.1% BSA. Assays were performed as described above except that 0.5 mM S-2765 was used as the substrate for FXa and the absorbance measurements were performed at 37° C. The assay buffer for FXa was 20 mM EPPS pH 8.2, 150 mM NaCl, 0.1% BSA, 25 mM EDTA.

Figure 2:
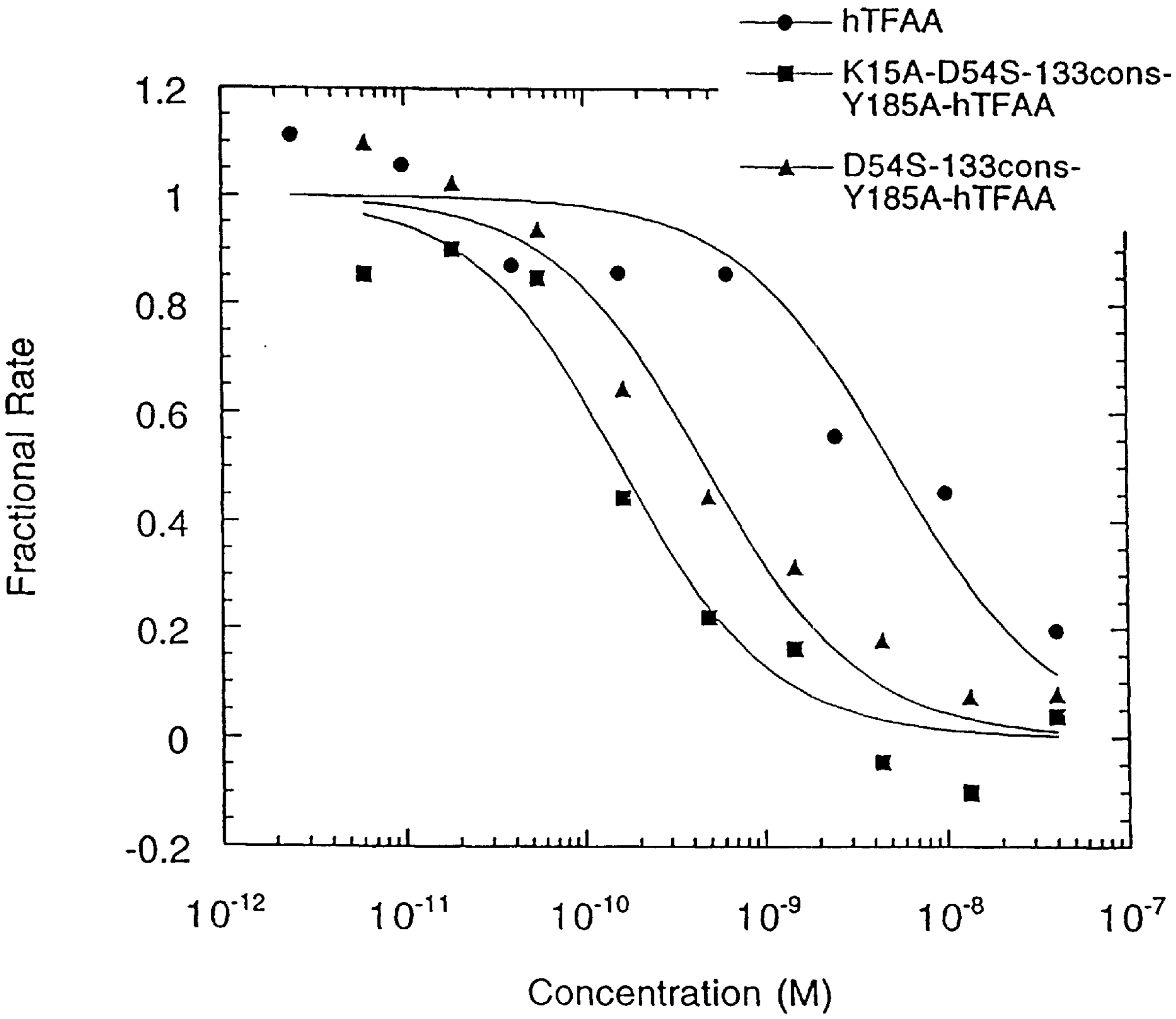
FIG. 2: The apparent equilibrium dissociation constant (Ki*) for inhibition of FX activation was determined from assays in which the inhibitor concentration was varied. Nonlinear regression analysis by using equation 1 was used to determine Ki* from these data. The data, and the curves calculated from the nonlinear regression analysis, are shown for hTFAA (SEQ ID NO: 3), Asp54Ser-133cons-Tyr185Ala-hTFAA (SEQ ID NO: 9), and Lys15Ala-Asp54Ser-133cons-Tyr185Ala-hTFAA (SEQ ID NO: 10) in FIG. 2.

The apparent equilibrium dissociation constant (Ki*) for inhibition of FX activation was determined from assays in which the inhibitor concentration was varied. A standard curve was constructed for Spectrozyme FXa hydrolysis by purified FXa (Hematech) such that the observed rate of hydrolysis for each time point could be converted into a concentration of FXa generated. These data were then analyzed by least squares linear regression to calculate the initial velocity of FXa generation for each concentration of inhibitor. Initial velocities were compared to the uninhibited rate to yield a fractional rate of FX activation for each inhibitor concentration. Nonlinear regression analysis by using equation 1 was used to determine Ki* from these data. The data, and the curves calculated from the nonlinear regression analysis, are shown for hTFAA, Asp54Ser-133cons-Tyr185Ala-hTFAA, and Lys15Ala-Asp54Ser-133cons-Tyr185Ala-hTFAA in FIG. 2.

These values, as well as the values for other hTFAA variants, are reported relative to the hTFAA value in Table IV.

TABLE IV

| hTFAA Variant | Ki* (hTFAA)/ Ki* (mutant) |
|---|---|
| hTFAA | 1 |
| Lys15Ala-hTFAA | 2.3 |
| Asp54Ser-hTFAA | 1.5 |
| Tyr185Ala-hTFAA | 2.2 |
| 133cons-hTFAA | 5.2 |
| Asp54Ser-133cons-hTFAA | 7.5 |
| Asp54Ser-133cons-Tyr185Ala-hTFAA | 11.5 |
| Lys15Ala-Asp54Ser-133cons-Tyr185Ala-hTFAA | 35.6 |

These results show that Lys15Ala-Asp54Ser-133cons-Tyr185Ala-hTFAA has a 36-fold increased affinity for FVIIa relative to the value measured for hTFAA. The affinity observed for this variant is nearly equivalent to that expected based on an additive contribution (Wells, (1990) Biochemistry 29:8509–8517 from the single-site mutations. Multiplication of the fold-increases in potency observed for the single-site mutations and the library 2 consensus sequence yields a calculated 40-fold increase in affinity.

Equation1: $V_1 / V_0 =$ $$1 - \frac{[E_0] + [I_0] + K_I^* - \sqrt{([E_0] + [I_0] + K_i^*)^2 - (4 \cdot [E_0] \cdot [I_0])}}{2 \cdot [E_0]}$$

In this equation $[E_0]$ is the enzyme concentration, $[I_0]$ is the inhibitor concentration, $V_i$ is the initial velocity of FXa generation in the presence of $[I_0]$ and $V_0$ is the initial velocity in the absence of inhibitor.

Example 4

Coagulation Assay

The inhibitory potency of hTFAA, Asp54Ser-133cons-Tyr185Ala-hTFAA, and Lys15Ala-Asp54Ser-133cons-Tyr185Ala-hTFAA were compared by adding a varied concentration of each inhibitor to plasma and measuring the prothrombin time (PT) using Innovin (Dade) human thromboplastin to initiate clotting. Clotting times were measured using the ACL 300 Research Coagulation Analyzer. For the prothrombin time (PT) assays, the incubation time was set at 120 sec and acquisition time at 600 sec. Citrated normal human plasma and inhibitor were incubated together for 10 minutes at room temperature prior to assay. A 100 $\mu$L portion of the sample (plasma and inhibitor) and 50 $\mu$L of thromboplastin solution were automatically mixed together after a 2 min incubation at 37° C. The clotting time was determined by optical assessment.

Figure 3:
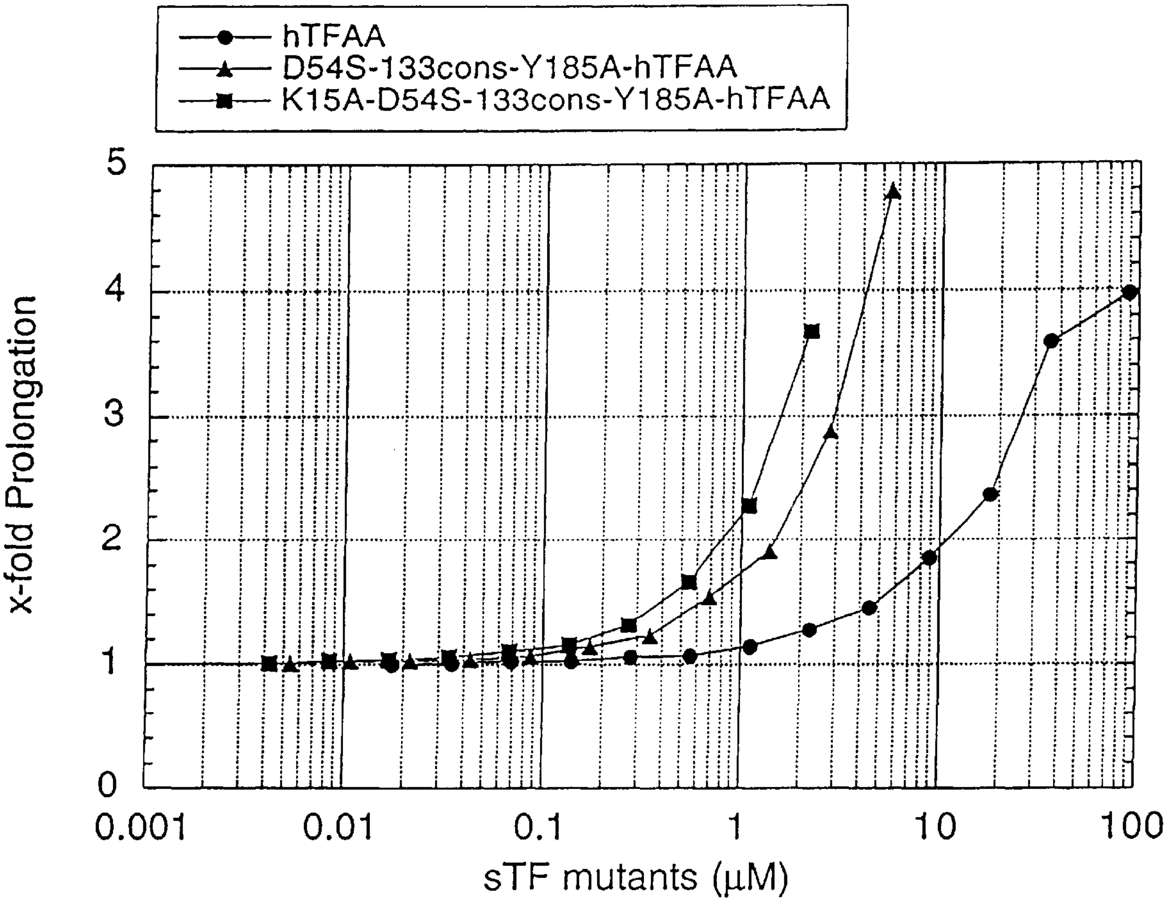
FIG. 3: Both Asp54Ser-133cons-Tyr185Ala-hTFAA (SEQ ID NO: 9) and Lys15Ala-AspSer-133cons-Tyr185Ala-hTFAA (SEQ ID NO: 10) gave a more potent inhibition of clotting than hTFAA (SEQ ID NO: 3) in the PT assay as shown in FIG. 3.

Both Asp54Ser-133cons-Tyr185Ala-hTFAA and Lys15Ala-Asp54Ser-133cons-Tyr185Ala-hTFAA gave a more potent inhibition of clotting than hTFAA in the PT assay as shown in FIG. 3. A two-fold prolongation of clotting time was obtained with 10 $\mu$M hTFAA, 1.5 $\mu$M S54–133cons-A185-hTFAA, or 0.8 $\mu$M A15-S54-133cons-A185-hTFAA.

These data show that increasing the affinity of hTFAA for FVIIa results in an increased anticoagulant effect.

Example 5

Determination of Antithrombotic Potential in a Rabbit Model of Deep Medial Injury Male New Zealand white rabbits (~4 kg) are anesthetized to surgical anesthesia plane with an IM injection of Ketamine/Xylaxine. The rabbits are placed supine on a restraining board, warmed to 37° C., and the neck and inner thigh area shaved. Teflon catheters are placed in a marginal ear vein and femoral artery for drug delivery(TF variants and controls) and sample collection respectively. Prior to treatment, blood samples are collected for coagulation tests (APTT and PT). Bleeding time is assessed from a cut made in the cuticle portion of a hind limb nail. Incisions are made in the neck region and the entire left common carotid artery and its branches are surgically isolated. An ultrasonic flow probe (Transonics®) is placed on the common carotid approximately 5 cm caudal to the common—internal bifurcation. After blood flow reaches a stable baseline, drugs (saline or test compounds) are delivered via the marginal ear vein. A deflated embolectomy catheter (Fogarty®, 3F) is then introduced into the lumen of the common carotid via an incision in the lingual branch. Blood flow through the artery is stopped briefly while the catheter is introduced and loosely secured with 2–0 silk tie at the incision site. After the catheter is in place and secure, blood flow is restored. The deflated balloon is advanced to within 2 mm of the flow probe and inflated with saline until resistance of the vessel wall is felt. The catheter is pulled back with a steady motion to the first branch and then deflated.

This procedure is repeated several times for each experimental animal, after which the catheter is removed. The ballooning procedure, from first insertion to removal of the catheter takes approximately 3 to 5 minutes and results in an area of damage that is 1.5 to 2 cm in length. Over 40 minutes, blood samples are taken for PT measurements, cuticle bleeding times are assessed and blood flow through the carotid monitored. Duration of patency is defined as the total amount of time (maximum=40 minutes) that any measurable blood flow is detected in the artery. Patency rate refers to the percentage of animals tested who had carotid artery blood flow ≧5 minutes.

At the end of the experiment, the rabbit is euthanized and the carotid artery removed and opened. If any thrombus is present, it is removed, blotted and the weight recorded.

What is claimed is:

1. A tissue factor protein variant comprising a human tissue factor protein comprising at least one amino acid substitution at a residue selected from the group consisting of Asp54 and Glu56, and at least one amino acid substitution at a residue selected from the group consisting of Glu 130, Arg 131, Leu133, Arg135 and Phe140, wherein the tissue factor protein variant has a greater affinity for FVII/FVIIa than does the human tissue factor protein and has about 90% sequence homology with a tissue factor protein having a sequence of SEQ ID NO: 1 or SEQ ID NO: 2.

2. The tissue factor protein variant of claim 1 wherein the amino acid residue substituted for Asp54 is selected from the group consisting of Lys, Asn, Glu, Ala and Ser, the amino acid residue substituted for Glu56 is selected from the group consisting of Asp, His, Gln, and Trp, the amino acid residue substituted for Leu133 is Ala, the amino acid residue substituted for Arg135 is selected from the group consisting of Trp, Gln, Leu, Tyr, Thr, and Ala, and the amino acid residue substituted for Phe140 is selected from the group consisting of Asn, His, Val, Ala, Arg and Gly.

3. The tissue factor protein variant of claim 2 wherein the amino acid residue substituted for Asp54 is Ser, the amino acid residue substituted for Arg135 is selected from the group consisting of Trp and Gln, and the amino acid residue substituted for Phe140 is Asn.

4. The tissue factor protein variant of claim 3 wherein amino acid residues Asp54, Glu 130, Arg 131, Leu133, and Phe140 are each substituted with another amino acid residue.

5. The tissue factor protein variant of claim 1 wherein the human tissue factor protein has a sequence of SEQ ID NO: 1 or SEQ ID NO: 2.

6. The tissue factor protein variant of claim 1 wherein the tissue factor protein variant further comprises at least one additional amino acid substitution at an amino acid residue selected from the group consisting of Lys 15, Asp44, Trp158, Ser163, Gly164, Lys165, Lys166, and Tyr 185.

7. The tissue factor protein variant of claim 6 wherein one of the amino acid residues is selected from the group consisting of Ser163 and Gly164.

8. The tissue factor protein variant of claim 7 wherein one of the amino acid residues is Ser163, and Ser63 is substituted with Ala.

9. The tissue factor protein variant of claim 6 wherein the human tissue factor protein has a sequence of SEQ ID NO: 1 or SEQ ID NO: 2.

10. A composition comprising the tissue factor protein variant of claim 1.

11. A composition comprising the tissue factor protein variant of claim 5.

12. A tissue factor protein variant comprising a human tissue factor protein comprising at least one amino acid substitution at a residue selected from the group consisting of Asp54, Glu56, Glu 130, Arg 131, Leu133, Arg135 and Phe140 and at least one amino acid substitution at a residue selected from the group consisting of Lys15, Gly164, Lys165, Lys166 and Tyr185, wherein the tissue factor protein variant has a greater affinity for FVII/FVIIa than does the human tissue factor protein and has about 90% sequence homology to a tissue factor protein having a sequence of SEQ ID NO: 1 or SEQ ID NO:2.

13. The tissue factor protein variant of claim 12 wherein the substituted amino acid residue for Lys15 and Tyr185 is Ala.

14. The tissue factor protein variant of claim 12 wherein the human tissue factor protein has a sequence of SEQ ID NO: 1 or SEQ ID NO: 2.

15. A tissue factor protein variant comprising a human tissue factor protein comprising amino acid substitutions at each of the residues Asp 54, Glu130, Arg131, Leu133, and Phe140, wherein the tissue factor protein variant has a greater affinity for FVII/FVIIa than does the human tissue factor protein and has about 90% sequence homology to a tissue factor protein having a sequence of SEQ ID NO: 1 or SEQ ID NO: 2.

16. The tissue factor protein of claim 15 wherein the amino acid residue substituted for Asp54 is Ser, the amino acid residue substituted for Glu130 is Asp, the amino acid residue substituted for Arg131 is Gln, the amino acid residue substituted for Leu133 is Ala, and the amino acid residue substituted for Phe140 is Asn.

17. The tissue factor protein of claim 16 further comprising an amino acid residue substitution at Lys15 wherein the substituted amino acid residue for Lys15 is Ala.

18. A tissue factor protein variant comprising a human tissue factor protein comprising at least one amino acid substitution at a residue selected from the group consisting of Asp54 and Glu56, and at least one amino acid substitution at a residue selected from the group consisting of Gly164, Lys165 and Lys166, wherein the tissue factor protein variant has a greater affinity for FVII/FVIIa than does the human tissue factor protein and has about 90% sequence homology to a tissue factor protein having a sequence of SEQ ID NO: 1 or SEQ ID NO: 2.

19. The tissue factor protein variant of claim 18 wherein the human tissue factor protein has a sequence of SEQ ID NO: 1 or SEQ ID NO: 2.

20. A tissue factor protein variant comprising a human tissue factor protein comprising at least one amino acid substitution at a residue selected from the group consisting of Glu130 and Arg131, and at least one amino acid substitution at a residue selected from the group consisting of Gly164, Lys165, Lys166 and Tyr185, wherein the tissue factor protein variant has a greater affinity for FVII/FVIIa than does the human tissue factor protein and has about 90% sequence homology to a tissue factor protein having a sequence of SEQ ID NO: 1 or SEQ ID NO: 2.

21. The tissue factor protein variant of claim 20 wherein the human tissue factor protein has a sequence of SEQ ID NO: 1 or SEQ ID NO: 2.

22. A tissue factor protein variant comprising a human tissue factor protein comprising amino acid substitutions at each of residues Glu130, Arg131, Leu133, Phe140, Lys 165 and Lys 166, wherein the tissue factor protein variant has a greater affinity for FVII/FVIIa than does the human tissue factor protein and has about 90% homology to a tissue factor protein having a sequence of SEQ ID NO: 1 or SEQ ID NO: 2.

23. The tissue factor protein variant of claim 22 wherein the human tissue factor protein has a sequence of SEQ ID NO: 1 or SEQ ID NO: 2.

24. A tissue factor protein variant according to claim 15, further comprising an amino acid substitutions at Lys 165 and Lys 166.

25. A tissue factor protein variant according to claim 24, further comprising an amino acid substitutions at Lys 15 and Tyr 185.

26. A tissue factor protein variant according to claim 25, further comprising an amino acid substitution at Asp 54.

27. A tissue factor protein variant comprising a tissue factor protein having the amino acid sequence of SEQ ID NO: 1 or SEQ ID NO: 2 with at least one amino acid substitution at an amino acid residue selected from the group consisting Glu130, Arg131, Leu133, Arg135, Phe140 and at least one amino acid substitution at a residue selected from group consisting of Lys15, Lys165, Lys166 and Tyr185, wherein the tissue factor protein variant has a greater affinity for FVII/FVIIa than does the tissue factor protein.

28. The tissue factor protein variant of claim 27, wherein each of the amino acids Gu130, Arg131, Leu133, and Phe140 are substituted.

29. The tissue factor protein variant of claim 27, wherein the amino acid residue substituted for Glu130 is Asp, the amino acid residue substituted for Arg131 is Gln, the amino acid residue substituted for Leu133 is Ala, and the amino acid residue substituted for Phe140 is Asn.

30. The tissue factor protein variant of claim 28, wherein each of the amino acids Lys 165 and Lys 166 are substituted.

31. The tissue factor protein variant of claim 30, further comprising an amino acid substitution at Asp 54.

32. The tissue factor protein variant of claim 31, wherein the amino acid Tyr 185 is substituted.

33. The tissue factor protein variant of claim 32, wherein tire amino acid Lys 15 is substituted.

34. A tissue factor protein variant comprising a human tissue factor protein having the amino acid sequence of SEQ ID NO: 1 or SEQ ID NO: 2 with at least one amino acid substitution at an amino acid residue selected from the group consisting of Asp54 and Glu56, and at least one amino acid substitution at a residue selected from the group consisting of Glu 130, Arg 131, Leu133, Arg135 and Phe140, wherein the tissue factor protein variant has a greater affinity for FVII/FVIIa than does the tissue factor protein.

35. The tissue factor protein variant of claim 34 wherein the amino acid residue substituted for Asp54 is selected from the group consisting of Lys, Asn, Glu, Ala and Set, the amino acid residue substituted for Glu56 is selected from the group consisting of Asp, His, Gin, and Trp, the amino acid residue substituted for Leu133 is Ala, the amino acid residue substituted for Arg135 is selected from the group consisting of Trp, Gln, Leu, Tyr, Thr, and Ala, and the amino acid residue substituted for Phe140 is selected from the group consisting of Asn, His, Val, Ala, Arg and Gly.

36. The tissue factor protein variant of claim 34 wherein the amino acid residue substituted for Asp54 is Ser, the amino acid residue substituted for Arg135 is selected from the group consisting of Trp and Gln, and the amino acid residue substituted for Phe140 is Asn.

37. The tissue factor protein variant of claim 34 wherein amino acid residues Asp54, Glu130, Arg131, Leu133, and Phe140 are each substituted with another amino acid residue.

38. The tissue factor protein variant of claim 34 wherein the tissue factor protein variant further comprises at least one additional amino acid substitution at an amino acid residue selected from the group consisting of Lys 15, Asp44, Trp158, Ser163, Gly164, Lys165, Lys166 and Tyr 185.

39. The tissue factor protein variant of claim 38 wherein one of the amino acid residues is selected from the group consisting of Ser163 and Gly164.

40. The tissue factor protein variant of claim 39 wherein one of the amino acid residues is Ser163, and Ser163 is substituted with Ala.

41. The tissue factor protein variant of claim 38 wherein each of amino acids Lys 165 and Lys 166 are substituted.

* * * * *